US010925578B2

United States Patent
Yamamoto

(10) Patent No.: US 10,925,578 B2
(45) Date of Patent: Feb. 23, 2021

(54) ACOUSTIC WAVE IMAGE GENERATING APPARATUS AND CONTROL METHOD THEREOF

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 519 days.

(21) Appl. No.: 15/660,240

(22) Filed: Jul. 26, 2017

(65) Prior Publication Data
US 2017/0319173 A1    Nov. 9, 2017

Related U.S. Application Data

(63) Continuation of application No. PCT/JP2016/057910, filed on Mar. 14, 2016.

(30) Foreign Application Priority Data

Mar. 23, 2015 (JP) .............................. JP2015-059623

(51) Int. Cl.
*A61B 8/14* (2006.01)
*A61B 8/12* (2006.01)
(Continued)

(52) U.S. Cl.
CPC ................. *A61B 8/14* (2013.01); *A61B 8/12* (2013.01); *G01S 7/52034* (2013.01);
(Continued)

(58) Field of Classification Search
CPC . A61B 8/14; A61B 8/12; A61B 8/4477–4494; G01S 15/892;
(Continued)

(56) References Cited

U.S. PATENT DOCUMENTS 4,920,573 A * 4/1990 Rhodes ................... G06T 11/60
378/21
4,930,514 A * 6/1990 Baba ........................ A61B 8/06
600/455

(Continued)

FOREIGN PATENT DOCUMENTS

JP        2-147052 A     6/1990
JP        5-154153 A     6/1993
(Continued)

OTHER PUBLICATIONS

Author Unkown, "Handbook of Ultrasonic Diagnostic Equipments," Corona Publishing Co., Ltd., Jan. 20, 1997, p. 76 (2 pages total).
(Continued)

*Primary Examiner* — Oommen Jacob
(74) *Attorney, Agent, or Firm* — Birch, Stewart, Kolasch & Birch, LLP

(57) ABSTRACT

There are provided an ultrasound image generating apparatus, which generates a high-quality ultrasound image even in a deep portion of a subject, and a control method thereof. In an ultrasound image (Img), for a portion (Ar1) equal to or less than a depth threshold value (D1), a real scanning line (L1) obtained from an acoustic wave echo signal is used. In the ultrasound image (Img), for a portion (Ar2) deeper than the depth threshold value (D1), an interpolation scanning line (L2) located between the real scanning lines (L1) is generated from an acoustic wave echo signal having a positional deviation between a focusing position of ultrasound waves and an observation target position. Also for a portion deeper than the interpolation scanning line (L2), a high-quality ultrasound image (Img) is obtained.

14 Claims, 23 Drawing Sheets

(51) Int. Cl.
*G01S 15/89* (2006.01)
*G01S 7/52* (2006.01)
*H04R 1/40* (2006.01)

(52) U.S. Cl.
CPC ...... *G01S 7/52036* (2013.01); *G01S 7/52044* (2013.01); *G01S 7/52095* (2013.01); *G01S 15/892* (2013.01); *H04R 1/40* (2013.01); *H04R 2201/405* (2013.01)

(58) Field of Classification Search
CPC ............. G01S 7/52034; G01S 7/52095; G01S 7/52036–52044; G01S 15/8915–8927; G01S 7/52085–52095; H04R 1/40; H04R 2201/405
USPC .................................. 600/425, 407, 437–461
See application file for complete search history.

(56) References Cited

U.S. PATENT DOCUMENTS

| | | | | |
|---|---|---|---|---|
| 5,327,257 A * | 7/1994 | Hrytzak | ............... | G06F 17/175 358/1.9 |
| 5,390,674 A * | 2/1995 | Robinson | ............ | G01S 7/52044 600/443 |
| 5,421,333 A * | 6/1995 | Takamizawa | ....... | G01S 7/52046 600/447 |
| 5,503,152 A * | 4/1996 | Oakley | ................... | A61B 8/08 128/916 |
| 5,528,302 A * | 6/1996 | Basoglu | .................. | A61B 8/06 348/163 |
| 5,544,655 A * | 8/1996 | Daigle | ................. | G01S 7/52095 600/447 |
| 5,570,691 A * | 11/1996 | Wright | ................ | G01S 7/52049 600/447 |
| 5,690,114 A * | 11/1997 | Chiang | .................. | A61B 8/463 600/447 |
| 5,735,282 A * | 4/1998 | Hossack | .................. | A61B 8/12 600/458 |
| 5,860,925 A * | 1/1999 | Liu | ..................... | G01S 7/52044 348/442 |
| 5,940,123 A * | 8/1999 | Daigle | ................ | G01S 7/52044 348/163 |
| 5,976,087 A * | 11/1999 | Resnick | .............. | G01S 7/52034 600/443 |
| 6,228,031 B1 * | 5/2001 | Hwang | ............... | G01S 7/52095 600/447 |
| 6,482,157 B2 * | 11/2002 | Robinson | ................. | A61B 8/00 600/437 |
| 7,918,797 B2 * | 4/2011 | Bae | .......................... | A61B 8/00 600/437 |
| 8,023,359 B2 * | 9/2011 | Miyaguchi | ................ | G06T 3/00 367/11 |
| 9,188,673 B2 * | 11/2015 | Ramamurthy | ........... | A61B 8/08 |
| 2001/0051772 A1 * | 12/2001 | Bae | ..................... | G01S 7/52034 600/447 |
| 2005/0156364 A1 * | 7/2005 | Bisiaux | .............. | G01N 29/2487 266/79 |
| 2006/0020207 A1 * | 1/2006 | Pagoulatos | ............... | A61B 8/13 600/456 |
| 2009/0043209 A1 | 2/2009 | Hirama | | |
| 2009/0264760 A1 * | 10/2009 | Lazebnik | ................. | A61B 8/08 600/447 |
| 2009/0275837 A1 * | 11/2009 | Shiina | .................... | A61B 8/485 600/459 |
| 2009/0326377 A1 * | 12/2009 | Hirama | ............... | G01S 7/52046 600/447 |
| 2010/0049042 A1 * | 2/2010 | Azuma | ..................... | A61B 8/00 600/437 |
| 2010/0085476 A1 * | 4/2010 | Hsu | ........................ | H04N 7/012 348/448 |
| 2010/0150412 A1 * | 6/2010 | Robinson | ............. | A61B 8/5276 382/128 |
| 2011/0016977 A1 * | 1/2011 | Guracar | ................... | A61B 8/54 73/606 |
| 2012/0053459 A1 * | 3/2012 | Eilers | ................... | A61B 8/0858 600/440 |
| 2013/0267851 A1 * | 10/2013 | Takahashi | ........... | G01S 15/8915 600/445 |
| 2013/0317361 A1 * | 11/2013 | Tabaru | ..................... | A61B 8/42 600/438 |
| 2014/0005548 A1 * | 1/2014 | Fraser | ................... | G01S 7/5202 600/447 |
| 2014/0343422 A1 * | 11/2014 | Waki | ...................... | A61B 8/483 600/438 |
| 2014/0355377 A1 * | 12/2014 | Hiriyannaiah | ........ | B06B 1/0215 367/7 |
| 2015/0293062 A1 * | 10/2015 | Kim | ..................... | G01S 15/8995 73/597 |
| 2017/0319173 A1 * | 11/2017 | Yamamoto | ............... | A61B 8/14 |

FOREIGN PATENT DOCUMENTS

| | | |
|---|---|---|
| JP | 2005-87266 A | 4/2005 |
| JP | 2009-28366 A | 2/2009 |
| WO | WO 2008/010366 A1 | 1/2008 |

OTHER PUBLICATIONS

Japanese Notification of Reasons for Refusal and English translation for Application No. 2017-508232, dated Apr. 24, 2018.
International Search Report for PCT/JP2016/057910 (PCT/ISA/210) dated May 16, 2017.
Written Opinion of the International Searching Authority for PCT/JP2016/057910 (PCT/ISA/237) dated May 17, 2016.

* cited by examiner

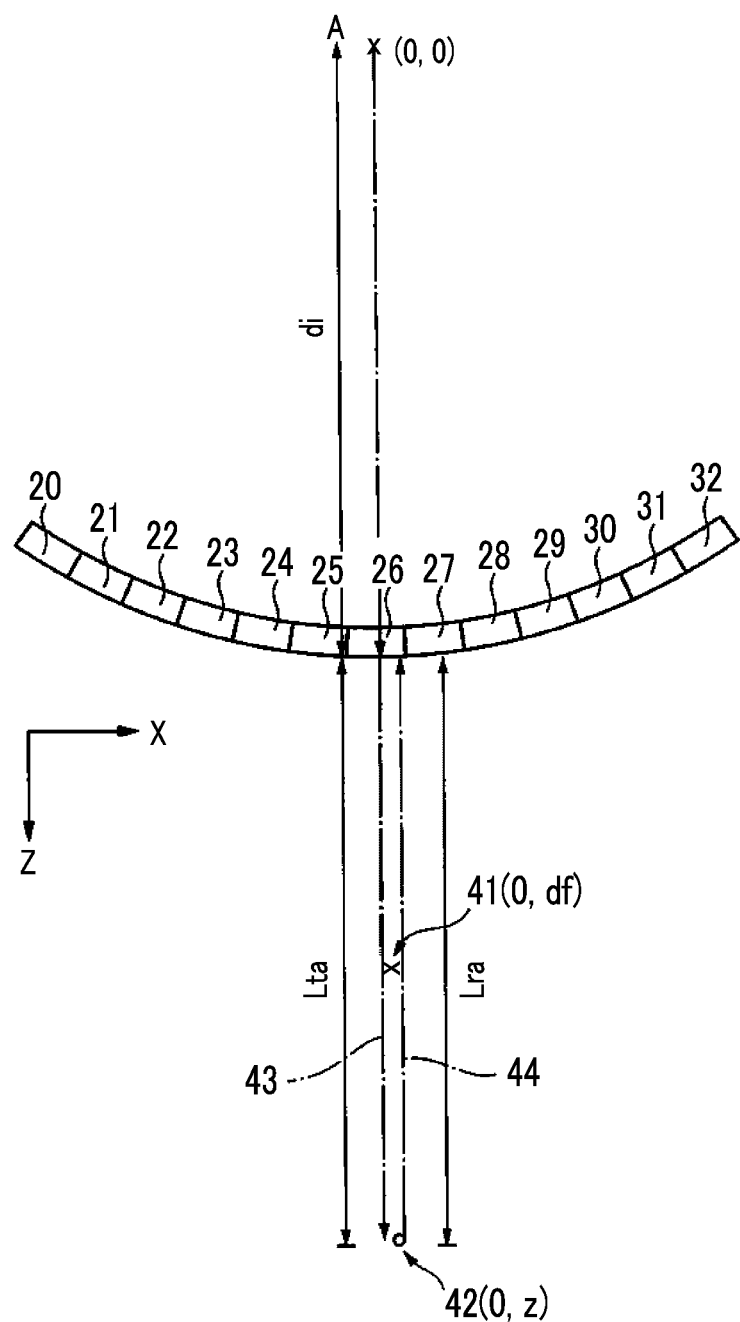

$$\sqrt{[(di+df)\sin\theta]^2 + [z-(di+df)\cos\theta]^2}$$

ACOUSTIC WAVE IMAGE GENERATING APPARATUS AND CONTROL METHOD THEREOF

CROSS-REFERENCE TO RELATED APPLICATIONS

This application is a Continuation of PCT International Application No. PCT/JP2016/057910 filed on Mar. 14, 2016, which claims priority under 35 U.S.C. § 119(a) to Japanese Patent Application No. 2015-059623 filed Mar. 23, 2015. Each of the above application(s) is hereby expressly incorporated by reference, in its entirety, into the present application.

BACKGROUND OF THE INVENTION

1. Field of the Invention

The present invention relates to an acoustic wave image generating apparatus and a control method thereof.

2. Description of the Related Art

In a convex probe for body surface and a micro convex type scope of an ultrasound endoscope, ultrasound waves transmitted from a plurality of ultrasound transducers are not parallel but have angles with a certain point as the center. For this reason, the density of scanning lines (scanning line interval) for generating an ultrasound image decreases in proportion to a portion of an ultrasound image showing a deep portion of a subject. In order to improve the image density of the portion of the ultrasound image showing the deep portion of the subject, there is a method of performing additional transmission a number of times by reducing the transmission interval of ultrasound waves in an arc direction in a portion far from the probe compared with a portion near the probe (JP1993-154153A (JP-H05-154153A)). In addition, there is a method of changing an ultrasound echo receiving method in a portion near the probe and an ultrasound echo receiving method in a portion far from the probe (JP1990-147052A (JP-H02-147052A)).

SUMMARY OF THE INVENTION

In the method disclosed in JP1993-154153A (JP-H05-154153A), however, since it takes time to perform additional transmission, the frame rate of the ultrasound image is lowered. As a result, the real-time property is lost. In the method disclosed in JP1990-147052A (JP-H02-147052A), since the ultrasound echo receiving method in a portion near the probe and the ultrasound echo receiving method in a portion far from the probe are different, the quality of an ultrasound image showing a deep portion of the subject may be different from the quality of an ultrasound image showing a shallow portion of the subject.

It is an object of the present invention to obtain a high-quality ultrasound image without lowering the frame rate even in an ultrasound image showing a deep portion of the subject.

An acoustic wave image generating apparatus according to the present invention comprises: an acoustic wave probe in which a plurality of acoustic wave transducers are arranged in an arc shape; a driving device (the driving device) for making the acoustic wave transducers transmit acoustic waves converging on a focusing position to a subject while updating the acoustic wave transducers for transmitting acoustic waves in a sequential manner; a real scanning line generation device (the real scanning line generation device) for generating real scanning lines indicating an acoustic wave image of the subject using an acoustic wave echo signal indicating an acoustic wave echo from an observation target position of the subject that is obtained based on driving of the acoustic wave transducers by the driving device; an interpolation scanning line generation device (the interpolation scanning line generation device) for generating a first interpolation scanning line located between the real scanning lines using the acoustic wave echo signal, which has a positional deviation in the arc direction between the focusing position and the observation target position, for a portion deeper than a depth threshold value in the subject; and an acoustic wave image generation device (the acoustic wave image generation device) for generating an acoustic wave image of the subject from the real scanning line and the first interpolation scanning line.

The present invention also provides an acoustic wave image generation method. That is, a control method of an acoustic wave image generating apparatus comprising an acoustic wave probe, in which a plurality of acoustic wave transducers are arranged in an arc shape, comprises: causing a driving device to make the acoustic wave transducers transmit acoustic waves converging on a focusing position to a subject while updating the acoustic wave transducers for transmitting acoustic waves in a sequential manner; causing a real scanning line generation device to generate real scanning lines indicating an acoustic wave image of the subject using an acoustic wave echo signal indicating an acoustic wave echo from an observation target position of the subject that is obtained based on driving of the acoustic wave transducers by the driving device; causing an interpolation scanning line generation device to generate a first interpolation scanning line located between the real scanning lines using the acoustic wave echo signal, which has a positional deviation in the arc direction between the focusing position and the observation target position, for a portion deeper than a depth threshold value in the subject; and causing an acoustic wave image generation device to generate an acoustic wave image of the subject from the real scanning line and the first interpolation scanning line.

The interpolation scanning line generation device may generate the first interpolation scanning line for a portion deeper than the depth threshold value in the subject using the acoustic wave echo signal, which is obtained from the portion deeper than the depth threshold value in the subject and which has a positional deviation in the arc direction between the focusing position and the observation target position.

The interpolation scanning line generation device may generate a second interpolation scanning line, which is located between the first interpolation scanning line generated by the interpolation scanning line generation device and the real scanning line, using the acoustic wave echo signal having a positional deviation in the arc direction between the focusing position and the observation target position.

The interpolation scanning line generation device may generate a second interpolation scanning line, which is located between the first interpolation scanning line generated by the interpolation scanning line generation device and the real scanning line, from the real scanning line and the first interpolation scanning line generated by the interpolation scanning line generation device.

The interpolation scanning line generation device may generate a second interpolation scanning line, which is located between the first interpolation scanning line generated by the interpolation scanning line generation device and the real scanning line, from the first interpolation scanning line generated by the interpolation scanning line generation device.

The acoustic wave image generating apparatus may further comprise a scanning line density calculation device for calculating a scanning line density of the real scanning lines for each depth of the subject. In this case, the interpolation scanning line generation device generates the first interpolation scanning line, for example, in a case where the scanning line density calculated by the scanning line density calculation device is equal to or less than a threshold value.

The interpolation scanning line generation device may generate the first interpolation scanning line of a different density for each depth until a scanning line density determined for each depth of the subject is obtained.

The acoustic wave image generating apparatus may further comprise a scanning line density calculation device for calculating a scanning line density of the real scanning lines for each depth of the subject. In this case, the interpolation scanning line generation device generates the first interpolation scanning line whose scanning line density is equal to or greater than a threshold value regardless of the depth of the subject.

The acoustic wave image generating apparatus may further comprise an acoustic wave image display control device for displaying the acoustic wave image generated by the acoustic wave image generation device on a display device.

The acoustic wave image generation device may generate the acoustic wave image from the real scanning line, the first interpolation scanning line, and the second interpolation scanning line.

The acoustic wave probe is, for example, a convex type acoustic wave probe.

The real scanning line may be generated using the acoustic wave echo signal having a positional deviation in the arc direction between the focusing position and the observation target position, or the real scanning line may be generated from the acoustic wave echo signal, which has a positional deviation in the arc direction between the focusing position and the observation target position, and the acoustic wave echo signal having no positional deviation.

According to the present invention, a plurality of acoustic wave transducers are arranged in the arc shape in the acoustic wave probe. Acoustic waves converging on the focusing position are transmitted from the acoustic wave transducers to the subject while the acoustic wave transducers for transmitting acoustic waves are being updated in a sequential manner. Real scanning lines indicating the acoustic wave image of the subject, which is generated using the acoustic wave echo signal indicating the acoustic wave echo from the observation target position of the subject, are generated. For a portion deeper than the depth threshold value in the subject, the first interpolation scanning line is generated using the acoustic wave echo signal having a positional deviation in the arc direction between the focusing position and the observation target portion. The acoustic wave image of the subject is generated from the real scanning line and the first interpolation scanning line. According to the present invention, since the first interpolation scanning line located between the real scanning lines is generated for a portion deeper than the threshold value and the acoustic wave image is generated using the real scanning line and the generated first interpolation scanning line, the quality of the acoustic wave image showing the deep portion of the subject is improved. In addition, since the reception method is not changed according to the depth of the subject, the real-time property of the acoustic wave image is also high.

BRIEF DESCRIPTION OF THE DRAWINGS

FIG. 8 shows transmission and reception of ultrasound waves.

DESCRIPTION OF THE PREFERRED EMBODIMENTS

In the present embodiment, an ultrasound wave is used as an acoustic wave. However, as long as an appropriate frequency is selected according to an object to be examined, measurement conditions, and the like, an acoustic wave having an audible frequency may be used without being limited to the ultrasound wave. In addition, not only can the present invention be used to diagnose the disease of a person as a subject, but also the present invention can be used to examine the contents of walls, piping, and the like by generating an acoustic wave image (ultrasound image).

Figure 1:
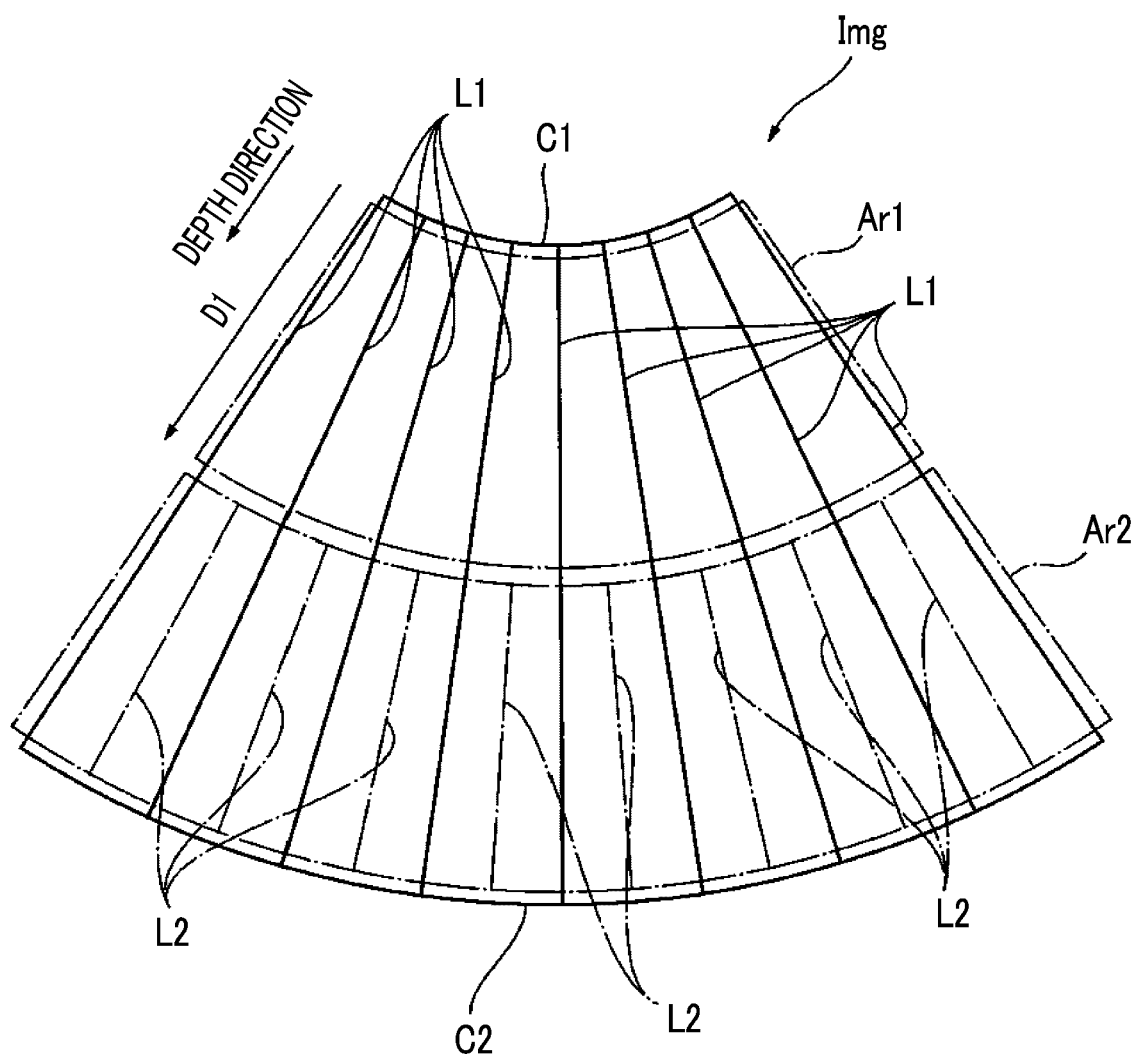
FIG. 1 is an example of an ultrasound image.

FIG. 1 is an example of an ultrasound image Img generated in an ultrasound diagnostic apparatus (acoustic wave image generating apparatus) according to an embodiment of the present invention.

In the ultrasound diagnostic apparatus according to the present embodiment, a convex type ultrasound probe (acoustic wave probe) in which a plurality of ultrasound transducers (acoustic wave transducers) are arranged in an arc direction is used. The ultrasound image Img obtained by using the convex type ultrasound probe is surrounded by a short arc C1 and a long arc C2 and straight lines connecting both ends of the two arcs C1 and C2 to each other. The direction from the short arc C1 to the long arc C2 indicates the depth direction of the subject.

By performing multi-line processing using the ultrasound echo signal indicating the ultrasound echo obtained from the subject based on the driving of the ultrasound transducers forming the ultrasound probe, a real scanning line L1 forming the ultrasound image Img is generated. For a portion deeper than a threshold value D1 in the depth direction, a first interpolation scanning line L2 located between the real scanning lines L1 is generated using the acoustic wave echo signal obtained by performing the multi-line processing. The ultrasound image Img is generated using the real scanning line L1 and the first interpolation scanning line L2.

The difference between the scanning line density (scanning line interval) in an ultrasound image portion Ar1 showing a shallow portion of the subject and the scanning line density in an ultrasound image portion Ar2 showing a deep portion of the subject is not changed significantly, the quality of the ultrasound image portion Ar1 showing the shallow portion of the subject and the quality of the ultrasound image portion Ar2 showing the deep portion of the subject are not changed. The quality of the ultrasound image portion Ar2 showing the deep portion of the subject is also improved.

Figure 2:
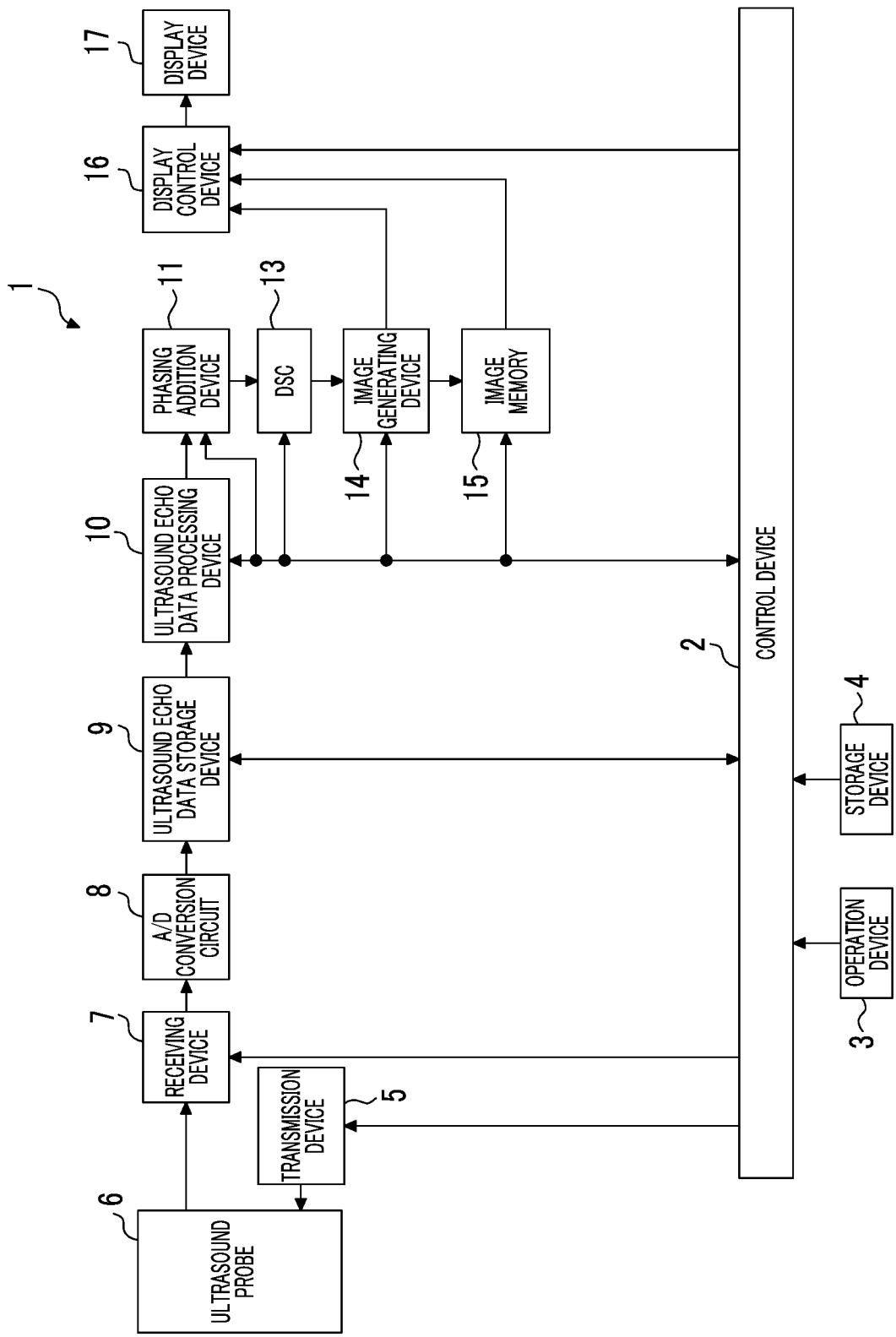
FIG. 2 is a block diagram showing the electric configuration of an ultrasound diagnostic apparatus.

FIG. 2 shows an embodiment of the present invention, and is a block diagram showing the electric configuration of an ultrasound diagnostic apparatus (acoustic wave image generating apparatus) 1.

First, a process of generating the above-described real scanning line L1 using the multi-line processing will be described.

The overall operation of the ultrasound diagnostic apparatus 1 is controlled by a control device 2.

An operation device 3, which is operated by a user (a doctor, a nurse, a technician, or the like) who operates the ultrasound diagnostic apparatus 1, and a storage device 4, in which predetermined data or the like is stored, are connected to the control device 2.

An ultrasound probe 6 is included in the ultrasound diagnostic apparatus 1. As described above, the ultrasound probe 6 is a convex type probe, and a plurality of ultrasound transducers are arranged in an arc shape (refer to FIG. 3A and the like).

A control signal output from the control device 2 is supplied to a transmission device 5. Then, an electrical pulse is supplied from the transmission device 5 to each ultrasound transducer of the ultrasound probe 6. The electrical pulse is converted into an ultrasound pulse 43 by the ultrasound transducer, the ultrasound pulse propagates through the body of the subject, and an ultrasound echo 44 returns to the ultrasound probe 6.

The ultrasound echo 44 is converted into an electrical signal (ultrasound echo signal) by the ultrasound transducer.

FIGS. 3A to 7B show a state in which the ultrasound pulse 43 is output from the ultrasound probe 6 and the ultrasound echo signal is obtained as described above.

Figure 3A:
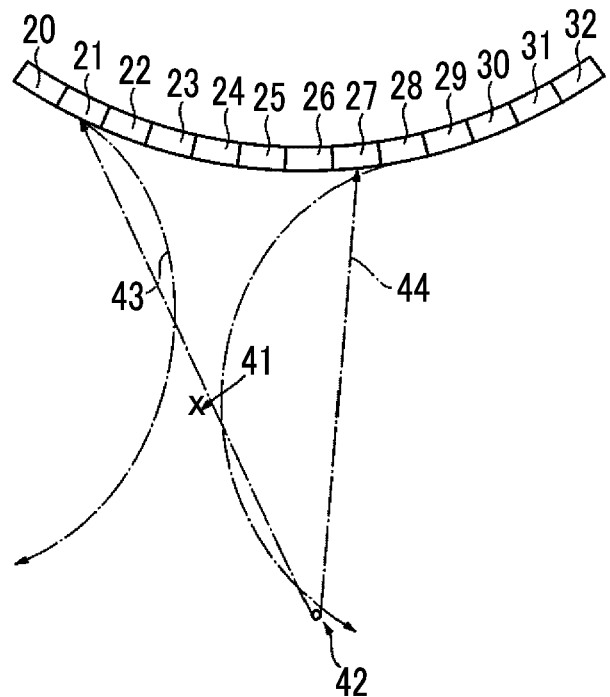
FIG. 3A shows transmission and reception of ultrasound waves.
Figure 4A:
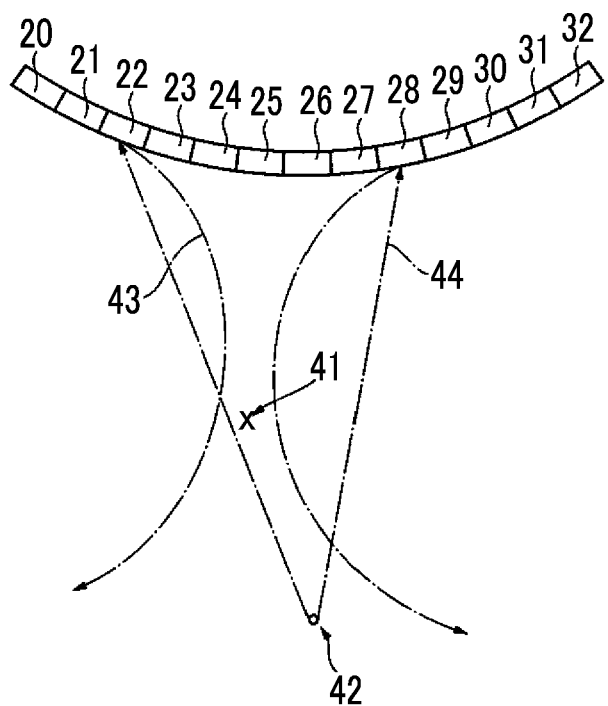
FIG. 4A shows transmission and reception of ultrasound waves.
Figure 5A:
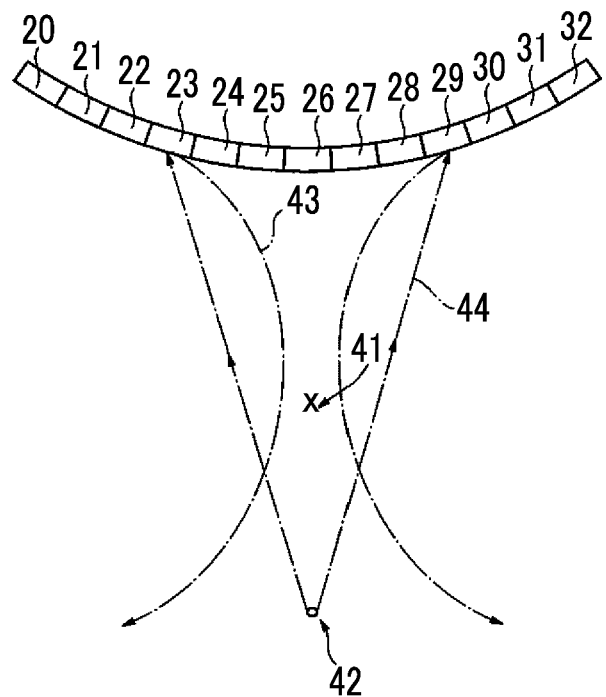
FIG. 5A shows transmission and reception of ultrasound waves.
Figure 6A:
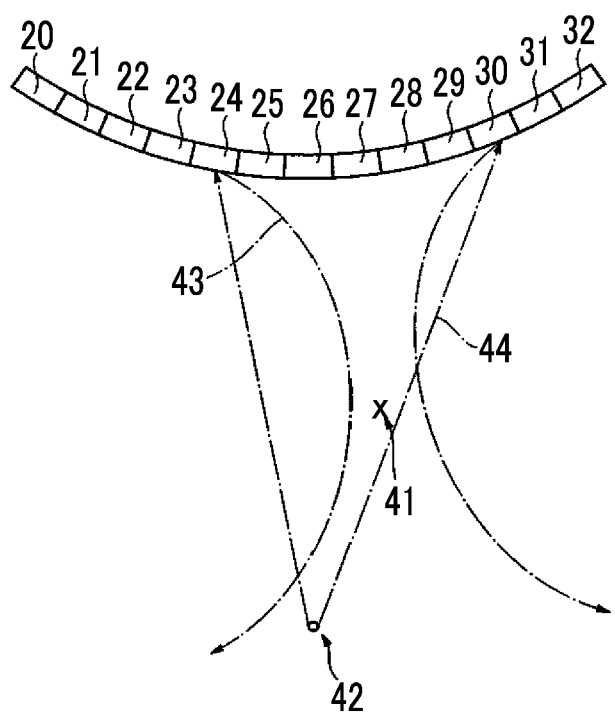
FIG. 6A shows transmission and reception of ultrasound waves.
Figure 7A:
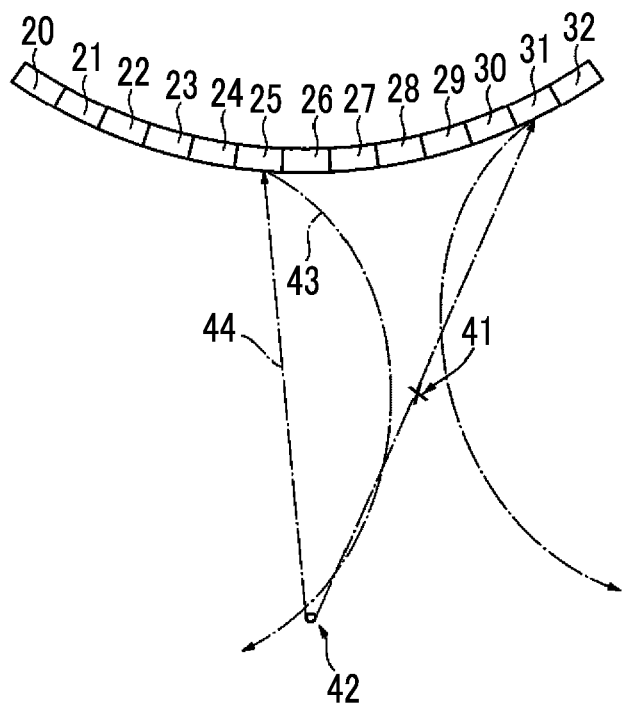
FIG. 7A shows transmission and reception of ultrasound waves.

FIG. 3A shows a state in which the ultrasound pulse 43 is output from ultrasound transducers 21 to 27 among ultrasound transducers 20 to 32 included in the ultrasound probe 6. FIG. 4A shows a state in which the ultrasound pulse 43 is output from ultrasound transducers 22 to 28 among the ultrasound transducers 20 to 32 included in the ultrasound probe 6. FIG. 5A shows a state in which the ultrasound pulse 43 is output from ultrasound transducers 23 to 29 among the ultrasound transducers 20 to 32 included in the ultrasound probe 6. FIG. 6A shows a state in which the ultrasound pulse 43 is output from ultrasound transducers 24 to 30 among the ultrasound transducers 20 to 32 included in the ultrasound probe 6. FIG. 7A shows a state in which the ultrasound pulse 43 is output from ultrasound transducers 25 to 31 among the ultrasound transducers 20 to 32 included in the ultrasound probe 6.

Thus, a plurality of ultrasound transducers 20 to 32 included in the ultrasound probe 6 are arranged in an arc shape (may be arranged in a two-dimensional manner). By the control device 2 (the driving device), the ultrasound pulse (acoustic wave) 43 converging on a focusing position 41 is transmitted from ultrasound transducers to be driven while the ultrasound transducers to be driven, among the ultrasound transducers 20 to 32, are being updated in a sequential manner.

Referring to FIG. 5A, it is assumed that the ultrasound pulse 43 is transmitted from the ultrasound transducers 23 to 29. The ultrasound pulse 43 is transmitted from the ultrasound transducers 23 to 29 so as to converge on the focusing position 41 at a predetermined distance in the transmission direction of the ultrasound transducer 26 (in FIG. 5A, directly below the ultrasound transducer 26) located at the center of the ultrasound transducers 23 to 29. Since the ultrasound pulse 43 is transmitted with a delay according to the positions of the ultrasound transducers 23 to 29, the ultrasound pulse 43 converges on the focusing position 41. In the example shown in FIG. 5A, an observation target position 42 (for example, a position where the medium changes in the subject) is present in the extension direction of the central ultrasound transducer 26 and the focusing position 41. For this reason, the ultrasound pulse 43 is emitted to the observation target position 42, and an ultrasound echo 44 is generated from the observation target position 42. The ultrasound echo 44 is received by the ultrasound transducers 23 to 29.

Figure 5B:
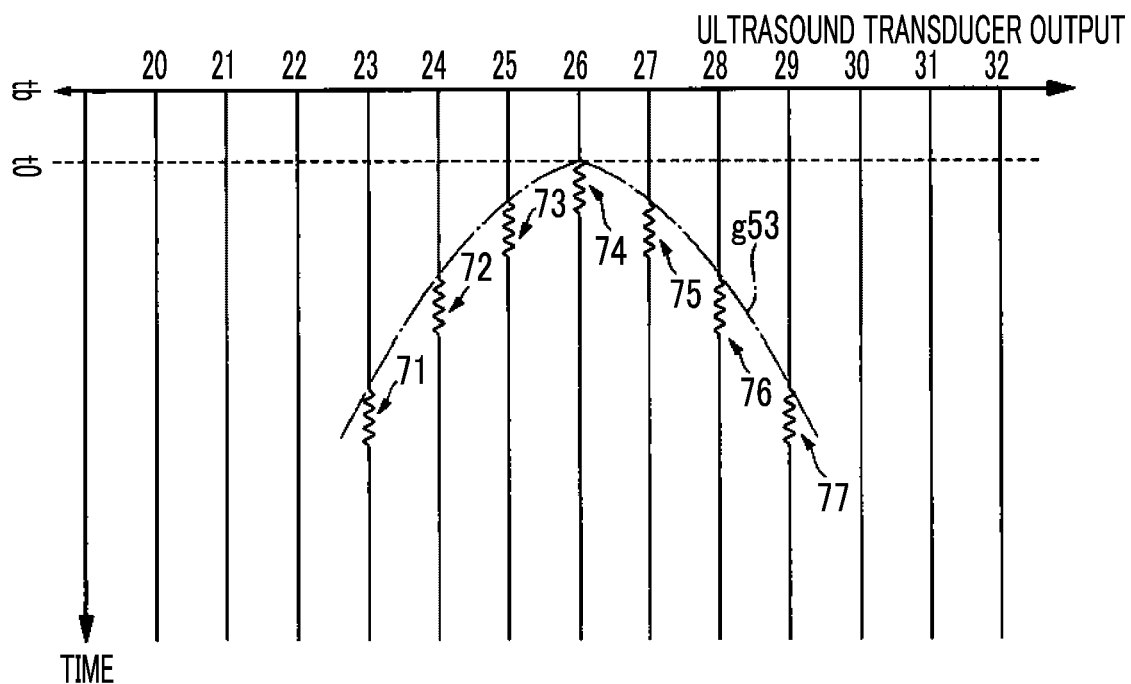
FIG. 5B shows an ultrasound echo signal.

FIG. 5B shows ultrasound echo signals 71 to 77 output from the ultrasound transducers 23 to 29 that have received the ultrasound echo 44. The horizontal axis indicates the position of the ultrasound transducer, and the vertical axis indicates the elapsed time from a time tb at which the ultrasound pulse 43 is output from the ultrasound transducer.

Since a difference between the propagation distances of the ultrasound pulse 43 and the ultrasound echo 44 occurs according to the positions of the ultrasound transducers 23 to 29 (since the ultrasound transducers 23 to 29 are arranged in an arc shape, distances to the focusing position 41 are different according to the positions of the ultrasound transducers 23 to 29 in the arc direction, and distances from the ultrasound transducer 26 to the ultrasound transducers 23, 24, 25, 27, 28, and 29 are also different), output timings of the ultrasound echo signals 71 to 77 output from the ultrasound transducers 23 to 29 are also different for each ultrasound transducer. The propagation distance of the ultrasound pulse 43 output from the central ultrasound transducer 26 and the propagation distance of the ultrasound echo 44 of the central ultrasound transducer 26 from the observation target position 42 are the shortest. Accordingly, the ultrasound echo signal 74 is first output from the central ultrasound transducer 26 (time t0). The propagation distance of the ultrasound pulse 43 output from the ultrasound transducers 25 and 27 on both sides of the central ultrasound transducer 26 and the propagation distance of the ultrasound echo 44 of the ultrasound transducers 25 and 27 from the observation target position 42 are the second shortest. Accordingly, the ultrasound echo signals 73 and 75 are output from the ultrasound transducers 25 and 27 after the ultrasound echo signal 74. Similarly, the ultrasound echo signals 72 and 76 are then output from the ultrasound transducers 24 and 28. Finally, the ultrasound echo signals 71 and 77 are output from the ultrasound transducers 23 and 29. In FIG. 5B (the same for the other diagrams), in order to show the ultrasound echo signals 71 and 77, an envelope of the ultrasound echo signals 71 to 77 is shown as an ultrasound echo signal group g53.

Referring to FIG. 3A, it is assumed that the ultrasound pulse 43 is transmitted from the ultrasound transducers 21 to 27. If the ultrasound pulse 43 converges on the focusing position 41 and does not spread exceeding the width of one ultrasound transducer (in the case shown in FIG. 3A, the ultrasound transducer 24), the ultrasound pulse 43 is not emitted to the observation target position 42 (for example, a position where the medium changes in the subject), which is not present in the extension direction of the central ultrasound transducer 24, among the ultrasound transducers 21 to 27 that transmit ultrasound waves, and the focusing position 41. Accordingly, no ultrasound echo 44 is generated from the observation target position 42. However, since the ultrasound pulse 43 spreads in a case where the ultrasound pulse 43 passes the focusing position 41, the ultrasound pulse 43 is also emitted to the observation target position 42 that is not present in the extension direction of the central ultrasound transducer 24 and the focusing position 41. Accordingly, the ultrasound echo 44 is generated from the observation target position 42. The ultrasound echo 44 is received by the ultrasound transducers 21 to 27.

Figure 3B:
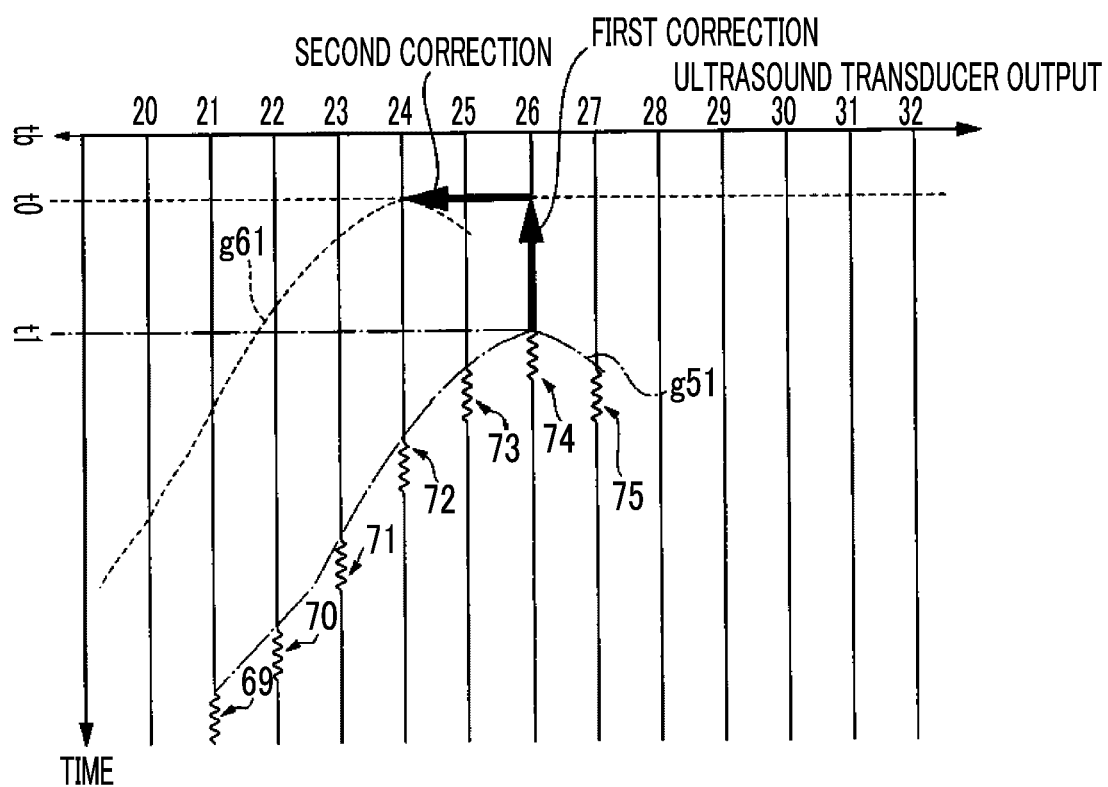
FIG. 3B shows an ultrasound echo signal.

FIG. 3B shows an ultrasound echo signal group g51 output from the ultrasound transducers 21 to 27 that receive the ultrasound echo 44. The ultrasound echo signal group g51 is an envelope of ultrasound echo signals 69 to 75 output from the ultrasound transducers 21 to 27 (in practice, the ultrasound echo signals are the ultrasound echo signals 69 to 75 in FIG. 3B). Since the observation target position 42 is present in the output direction (in FIG. 3A, directly below) of the ultrasound pulse 43 of the ultrasound transducer 26 among the ultrasound transducers 21 to 27 that receive the ultrasound echo 44, the ultrasound echo signal 74 is first output from the ultrasound transducer 26 (time t1). Then, the ultrasound echo signals 73 and 75 are output from the ultrasound transducers 25 and 27, respectively, and then the ultrasound echo signal 72 is output from the ultrasound transducer 24. In addition, the ultrasound echo signal 71 is output from the ultrasound transducer 23, the ultrasound echo signal 70 is output from the ultrasound transducer 22, and the ultrasound echo signal 69 is output from the ultrasound transducer 21. Since the focusing position 41 is not present between the observation target position 42 and the ultrasound transducer 26 that receives the ultrasound echo 44, the time t1 at which the ultrasound echo signal 74 is first output is later than the time t0 at which the ultrasound echo signal 74 is first output as shown in FIG. 5B.

Referring to FIG. 4A, it is assumed that ultrasound transducers to be driven are updated and the ultrasound pulse 43 is transmitted from the ultrasound transducers 22 to 28. In the same manner as described with reference to FIG. 3A, the ultrasound echo 44 is received by the ultrasound transducers 22 to 28.

Figure 4B:
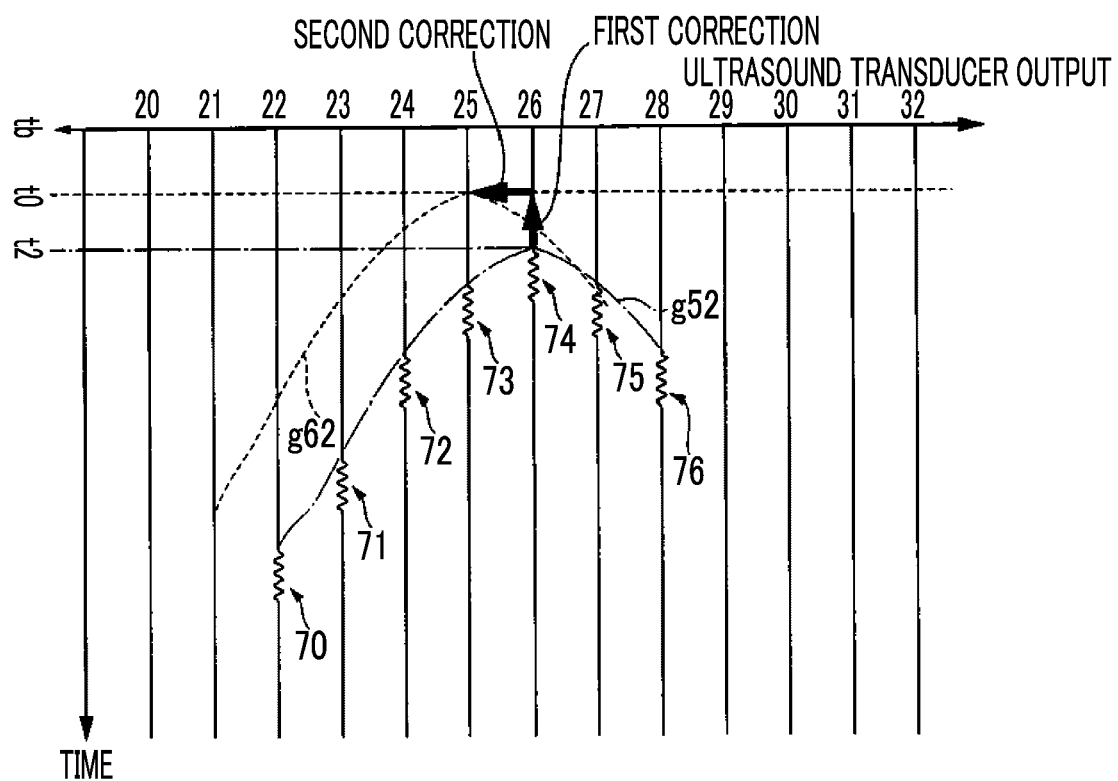
FIG. 4B shows an ultrasound echo signal.

Referring to FIG. 4B, an ultrasound echo signal group g52 is obtained from the ultrasound transducers 22 to 28 in the same manner as in FIG. 3B. The ultrasound echo signal group g52 is also an envelope of ultrasound echo signals 70 to 76 output from the ultrasound transducers 22 to 28. In the same manner as described above, the ultrasound echo signal 74 is first output from the ultrasound transducer 26 (time t2).

In a case where ultrasound transducers to be driven are updated and the ultrasound pulse 43 is transmitted from the ultrasound transducers 23 to 29 as shown in FIG. 5A, the operation is the same as that already described.

Referring to FIG. 6A, it is assumed that ultrasound transducers to be driven are updated and the ultrasound pulse 43 is transmitted from the ultrasound transducers 24 to 30. In the same manner as described above, the ultrasound echo 44 is received by the ultrasound transducers 24 to 30.

Figure 6B:
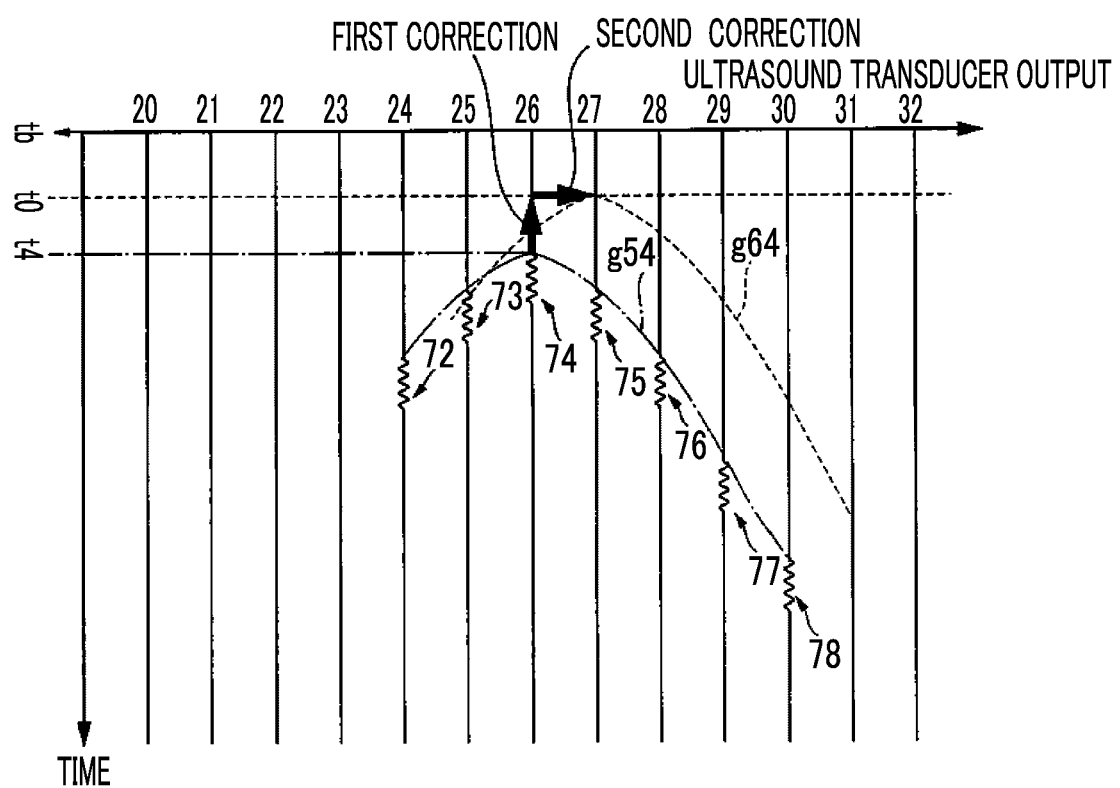
FIG. 6B shows an ultrasound echo signal.

Referring to FIG. 6B, an ultrasound echo signal group g54 is obtained from the ultrasound transducers 24 to 30 in the same manner as in FIG. 3A and the like. The ultrasound echo signal group g54 is also an envelope of ultrasound echo signals 72 to 78 output from the ultrasound transducers 24 to 30. In the same manner as described above, the ultrasound echo signal 74 is first output from the ultrasound transducer 26 (time t4).

Referring to FIG. 7A, it is assumed that ultrasound transducers to be driven are updated and the ultrasound pulse 43 is transmitted from the ultrasound transducers 25 to 31. In the same manner as described with reference to FIG. 3A, the ultrasound echo is received by the ultrasound transducers 25 to 31.

Figure 7B:
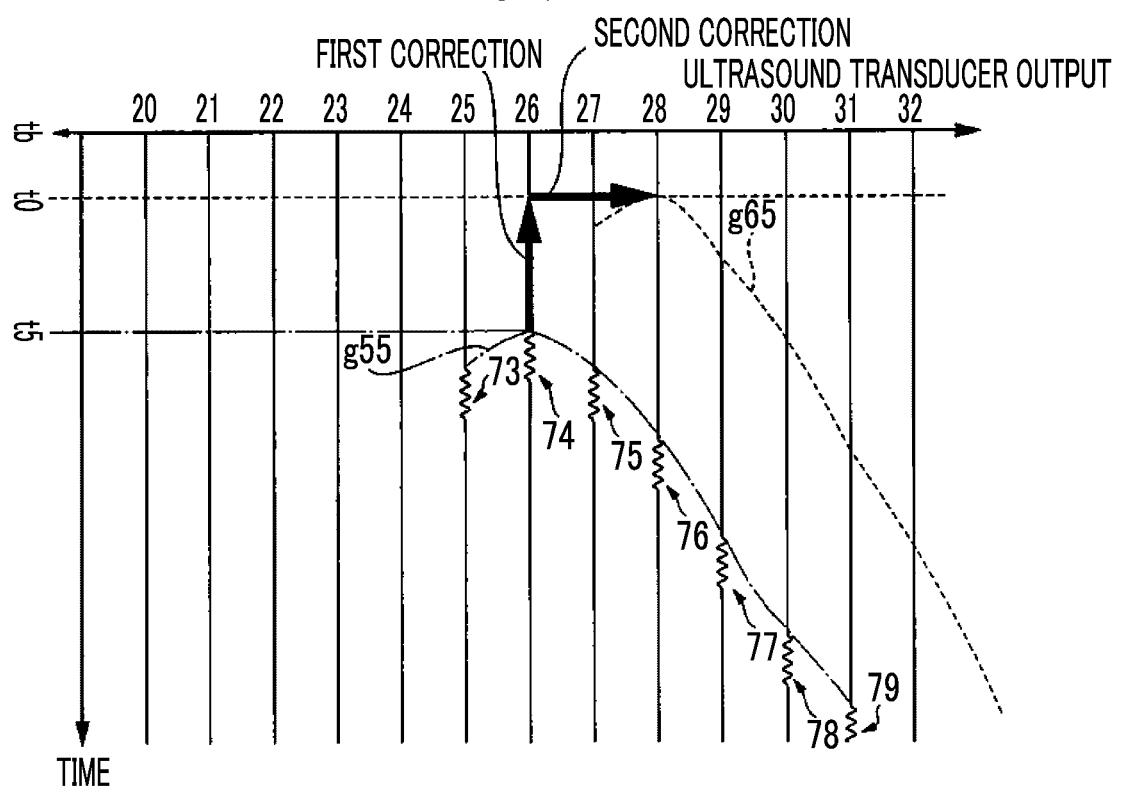
FIG. 7B shows an ultrasound echo signal.

Referring to FIG. 7B, an ultrasound echo signal group g55 is obtained from the ultrasound transducers 25 to 31 in the same manner as in FIG. 3A and the like. The ultrasound echo signal group g55 is also an envelope of ultrasound echo signals 73 to 79 output from the ultrasound transducers 25 to 31. In the same manner as described above, the ultrasound echo signal 74 is first output from the ultrasound transducer 26 (time t5).

Referring back to FIG. 2, the ultrasound echo signals obtained as described above are supplied to a reception device 7. The ultrasound echo signal is amplified by the reception device 7, and is converted into digital ultrasound echo data by an analog/digital (A/D) conversion circuit 8. The ultrasound echo data is supplied to an ultrasound echo data storage device 9 so as to be temporarily stored therein. The ultrasound echo data is read from the ultrasound echo data storage device 9, and is input to an ultrasound echo data processing device 10.

In the ultrasound echo data processing device 10, among ultrasound echo signals (acoustic wave echo signals) that are output from ultrasound transducers (acoustic wave transducers) due to the ultrasound transducers (acoustic wave transducers) receiving the ultrasound echo (acoustic wave echo) 44 of the observation target position 42 of the subject obtained based on the driving of the ultrasound transducers (acoustic wave transducers) by the control device 2 (the driving device), as shown in FIGS. 3A, 4A, 6A, and 7A, for ultrasound echo data (acoustic wave signal) having a positional deviation in the arc direction between the focusing position 41 and the observation target position 42, the positional deviation is corrected according to the position of the ultrasound transducer to be driven.

As will be described later, the correction of positional deviation is to generate an ultrasound echo signal obtained in a case where it is assumed that the observation target position 42 is present between the focusing position 41 and the ultrasound transducer 24 located at the center of the ultrasound transducers 21 to 27 that receive the ultrasound echo 44 from the observation target position 42. In other words, the correction of positional deviation is to generate an ultrasound echo signal obtained in a case where it is assumed that the ultrasound pulse 43 is transmitted and the observation target position 42 is present on the extension of the focusing position 41 and the ultrasound transducer 24 located at the center of the ultrasound transducers 21 to 27 that receive the ultrasound echo 44.

Referring to FIG. 3B, in the ultrasound echo data processing device 102, first correction is performed in order to correct the delay time so that the ultrasound echo signal group g51 is output from the ultrasound transducer 26 at the time t0 as shown in FIG. 5B, and second correction is performed in order to shift the apex of the ultrasound echo signal group g51 so that the positional deviation in the arc direction between the focusing position 41 and the observation target position 42 is eliminated. The positional deviation in the arc direction is a deviation between the focusing position 41 and the observation target position 42 in the arc direction. The correction of the positional deviation in the arc direction is to generate an ultrasound echo signal, which can be obtained in a case where there is no positional deviation in the arc direction, in a case where there is a positional deviation in the arc direction between the focusing position 41 and the observation target position 42 as shown in FIG. 3A (in a case where the focusing position 41 and the observation target position 42 are not present on a straight line in a direction perpendicular to the arc direction). In the case shown in FIG. 3A, the focusing position 41 and the observation target position 42 are shifted from each other by a distance of two ultrasound transducers in the arc direction. Accordingly, the ultrasound echo signal group g51 is shifted by the distance of two ultrasound transducers in a direction opposite to the arc direction (a direction from the ultrasound transducer 20 to the ultrasound transducer 32 is defined as the arc direction) so that the deviation of the distance is eliminated. A combination of the first correction and the second correction is positional deviation correction. Therefore, as shown in FIG. 3B, the ultrasound echo signal group g51 (hereinafter, the ultrasound echo signal may be referred to as ultrasound echo data) is corrected to an ultrasound echo data group g61 as shown by the dotted line. Thus, in the ultrasound echo data processing device 102, among the pieces of ultrasound echo data that are output from the ultrasound transducers 21 to 27 due to the ultrasound transducers 21 to 27 receiving the ultrasound echo 44 of the observation target position 42 of the subject obtained based on the driving of the ultrasound transducers by the control device (the driving device) 2, for ultrasound echo data having a positional deviation in the arc direction between the focusing position 41 and the observation target position 42, the positional deviation is corrected according to the position of the ultrasound transducer to be driven by the control device 2.

The delay time in the first correction can be calculated as follows.

FIG. 8 shows the ultrasound pulse 43 and the ultrasound echo 44 in a case where there is no positional deviation in the arc direction (one direction) between the focusing position 41 and the observation target position 42 as shown in FIG. 5A.

As shown in FIG. 8, it is assumed that one direction is an X direction and a direction perpendicular to the one direction is a Z direction. It is assumed that a plurality of ultrasound transducers 23 to 29 are arranged in an arc direction at positions of a radius di from the center indicated by reference numeral A. It is assumed that the X and Z coordinates of the center position A are $(X, Z)=(0, 0)$, the coordinates of the focusing position 41 are $(X, Z)=(0, df)$, and the coordinates of the observation target position 42 are $(X, Z)=(0, z)$. In a case where there is no positional deviation in the arc direction between the focusing position 41 and the observation target position 42, the length Lta of a transmission path until the ultrasound pulse 43 transmitted from the ultrasound transducer 26 reaches the observation target position 42 through the focusing position 41 is equal to the length Lra of a receiving path until the ultrasound echo 44 reflected from the observation target position 42 returns to the ultrasound transducer 26 from the observation target position 42. Accordingly, since $Lta=Lra=z-di$ is satisfied, a propagation distance Lua obtained by adding up the propagation distance Lta of the ultrasound pulse 43 and the propagation distance Lra of the ultrasound echo 44 is $Lua=Lta+Lra=2z-2di$. By dividing the propagation distance Lua obtained as described above by the speed of sound (speed of sound in the subject), the propagation time of the ultrasound pulse 43 and the ultrasound echo 44 in a case where there is no positional deviation is obtained.

Figure 9:
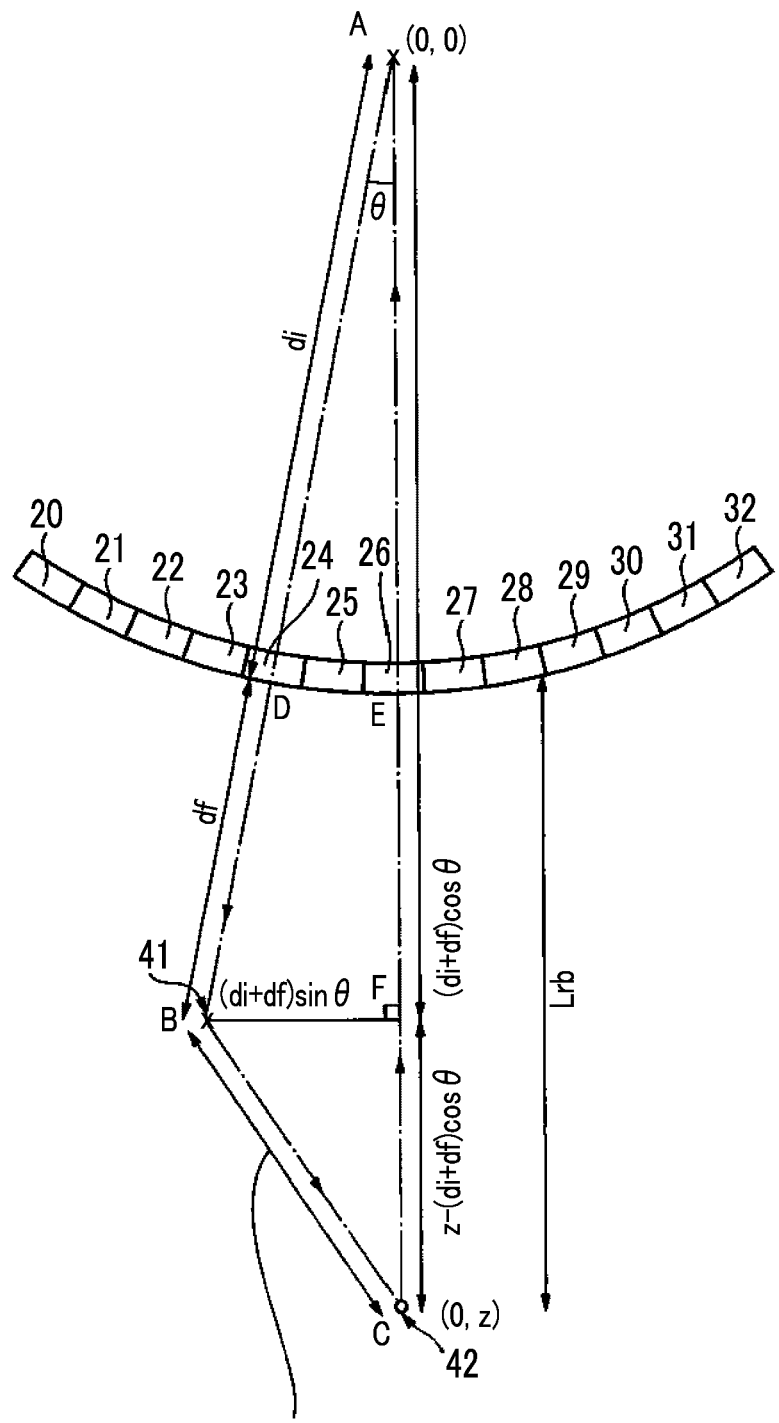
FIG. 9 shows transmission and reception of ultrasound waves.

FIG. 9 shows the ultrasound pulse 43 and the ultrasound echo 44 in a case where there is a positional deviation in the arc direction between the focusing position 41 and the observation target position 42 as shown in FIG. 3A.

The focusing position 41 is on the extension line of the center position A and the center of the ultrasound transducer 24, and is shifted in the arc direction (in FIG. 9, assuming that the direction from the left side to the right side is a positive arc direction, a negative arc direction) from the observation target position 42. It is assumed that the length of a transmission path until the ultrasound pulse 43 transmitted from the ultrasound transducer 24 reaches the observation target position 42 through the focusing position 41 is Ltb and the length of a receiving path until the ultrasound echo 44 reflected from the observation target position 42 returns to the ultrasound transducer 26 from the observation target position 42 is Lrb. Assuming that the center position of the arc of the ultrasound transducers 20 to 32 arranged in an arc shape (center position of the circle in a case where the ultrasound transducers 20 to 32 are arranged on the circumference) is A, the focusing position 41 is B, the observation target position 42 is C, the center position of the ultrasound transducer 24 is D, the center position of the ultrasound transducer 26 is E, and a point where a perpendicular drawn from the focusing position 41 to the side CA in a triangle ABC crosses the side CA is F, the length Ltb of the transmission path is a distance between DB+a distance between BC, and the length Lrb of the receiving path is a distance between CE. The distance between DB is df, and the distance between BC is $\sqrt{\{(\text{distance between BF})^2 + (\text{distance between CF})^2\}}$. Assuming that the angle formed by the ultrasound transducer 24 and the ultrasound transducer 26 is $\theta$, the distance between BF is $(di+df)\sin\theta$, and the distance between CF is (distance between AC)−(distance between AF) and accordingly $z-(di+df)\cos\theta$. Therefore, the distance between BC is $\sqrt{[\{(di+df)\sin\theta\}^2+\{z-(di+df)\cos\theta\}^2]}$. The distance between CE is z−di. The propagation distance Lub obtained by adding up the propagation distance Ltb of the ultrasound pulse 43 and the propagation distance Lrb of the ultrasound echo 44 is Lub=Ltb+Lrb=df+$\sqrt{[\{(di+df)\sin\theta\}^2+\{z-(di+df)\cos\theta\}^2]}$+z−di. By dividing the propagation distance Lub obtained as described above by the speed of sound, the propagation time of the ultrasound pulse 43 and the ultrasound echo 44 in a case where there is a positional deviation is obtained.

From the difference between the propagation time in a case where there is no positional deviation and the propagation time in a case where there is a positional deviation, the delay time to be corrected in the first correction is calculated as described above. It is needless to say that the delay time can be similarly calculated in the cases of positional deviation shown in FIGS. 4A, 6A, 7A, and the like as well as in the case of positional deviation shown in FIG. 3A.

Similarly, for the ultrasound echo data groups g52, g54, and g55 in which a positional deviation in the arc direction occurs between the focusing position 41 and the observation target position 42 as in FIGS. 4B, 6B, and 7B, positional deviation correction is performed by the ultrasound echo data processing device 10, and ultrasound echo data groups g62, g64, and g65 for which the positional deviation has been corrected are obtained.

Then, the ultrasound echo data groups g61, g62, g64, and g65 for which the positional deviation has been corrected and the ultrasound echo data group g53 without positional deviation are superimposed by the ultrasound echo data processing device 10 so that the same pieces of ultrasound echo data are added up.

In the superimposition, superimposition is performed so that the position of the ultrasound transducer 26 on the extension line of the observation target position 42 overlaps ultrasound echo data 74. The superimposed pieces of ultrasound echo data 69 to 79 are supplied to a phasing addition device 11.

Figure 10:
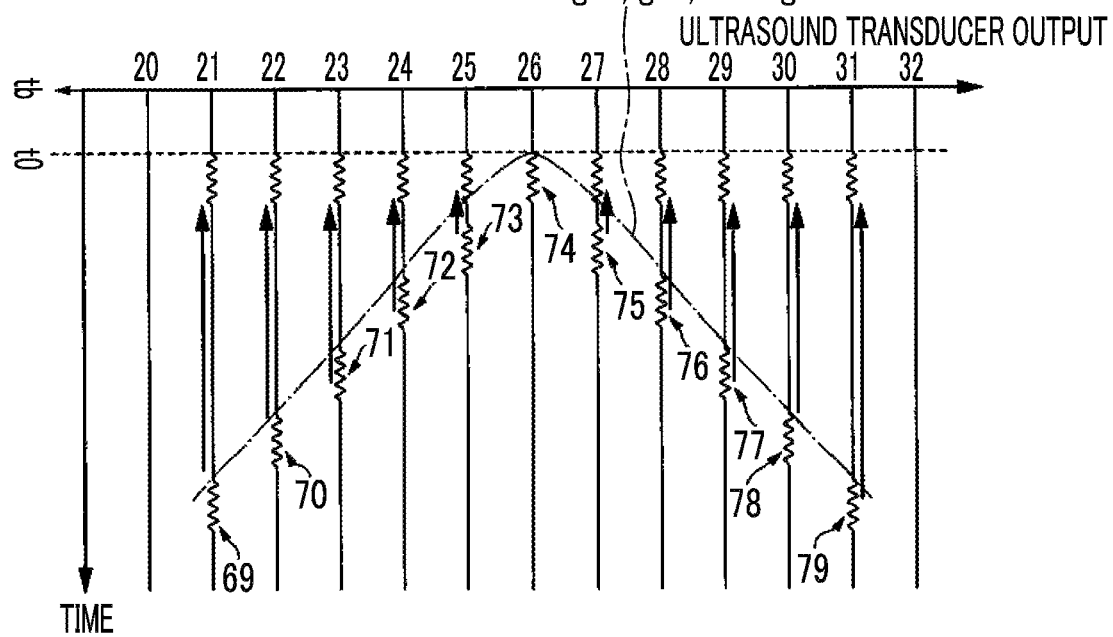
FIG. 10 shows a part of processing for phasing addition.
Figure 11:
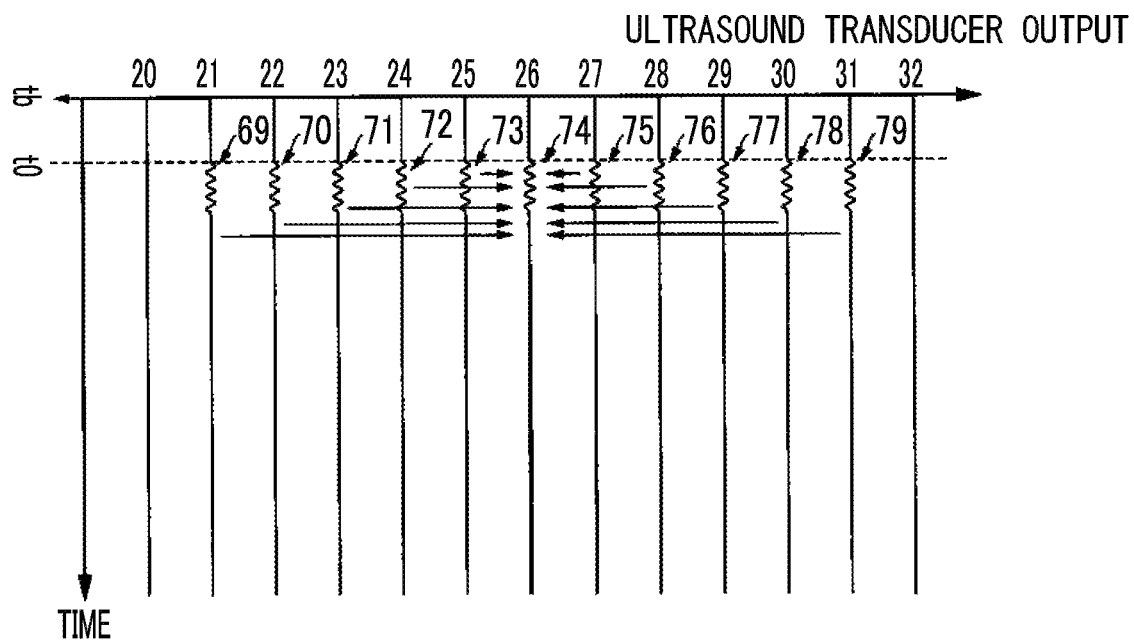
FIG. 11 shows a part of processing for phasing addition.

FIGS. 10 and 11 show a state in which the superimposed pieces of ultrasound echo data 69 to 79 are subjected to phasing addition.

Referring to FIG. 10, output time correction is performed by the phasing addition device 11 so that the output time of the superimposed pieces of ultrasound echo data 69 to 79 becomes the same as the output timing of the ultrasound echo signal 74 that is first output from the ultrasound transducer 26 at time t0.

Then, referring to FIG. 11, the pieces of ultrasound echo data 69 to 79 having been subjected to the output time correction are added up by the phasing addition device 11 so as to be superimposed at the position of the ultrasound transducer 26 on the extension line of the observation target position 42. By this addition, ultrasound echo data indicating the real scanning line (in this case, a real scanning line corresponding to the ultrasound transducer 26) L1 is obtained.

Such output time correction and addition of the pieces of ultrasound echo data 69 to 79 are phasing addition, and are performed by the phasing addition device 11 as described above. By performing the phasing addition, the S/N ratio is improved.

Here, the ultrasound echo data groups g61, g62, g64, and g65 for which the positional deviation has been corrected and the ultrasound echo data group g53 for which no positional deviation has been corrected are subjected to phasing addition after being superimposed. However, the order is not limited thereto. That is, the ultrasound echo data groups g61, g62, g64, and g65 for which the positional deviation has been corrected and the ultrasound echo data group g53 for which no positional deviation has been corrected may be independently subjected to phasing addition and then be superimposed to obtain a piece of superimposed data. In addition, at least some of the ultrasound echo data groups g61, g62, g64, and g65 for which the positional deviation has been corrected and the ultrasound echo data group g53 for which no positional deviation has been corrected may be superimposed after being weighted by the ultrasound echo data processing device 10 or the like. The processing of generating scanning lines by performing phasing addition of the ultrasound echo data groups g61, g62, g64, and g65 for which the positional deviation has been corrected as described above is the multi-line processing. In the multi-line processing, the ultrasound echo data group g53 for which no positional deviation has been corrected may be used, or may not be used.

Since the phasing addition is performed in this manner, the real scanning line L1 indicating the ultrasound image Img is generated, as shown in FIG. 1, using the ultrasound echo data processing device 10 and the phasing addition device 11 (the real scanning line generation device). In the example described above, the real scanning line L1 corresponding to the position of the ultrasound transducer 26 is generated.

Next, a process of generating the first interpolation scanning line L2 using the multi-line processing will be described. A case will be described in which the first interpolation scanning line L2 positioned between the ultrasound transducers 26 and 27 is generated. However, the first interpolation scanning line L2 positioned at other places can be similarly generated. The following process is performed in the ultrasound echo data processing device 10.

Figure 12A:
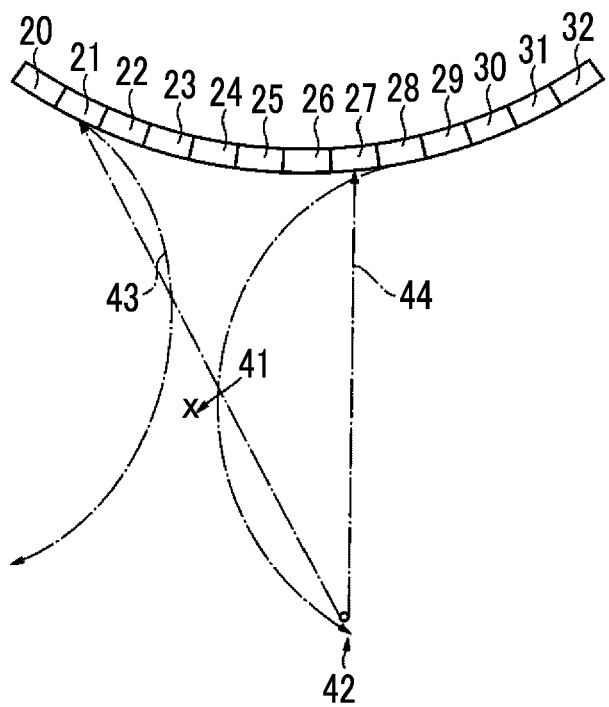
FIG. 12A shows transmission and reception of ultrasound waves.
Figure 13A:
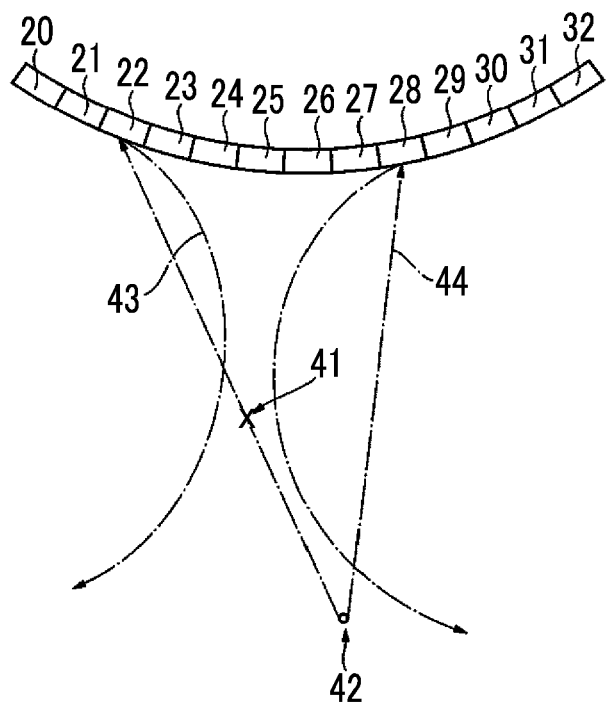
FIG. 13A shows transmission and reception of ultrasound waves.
Figure 14A:
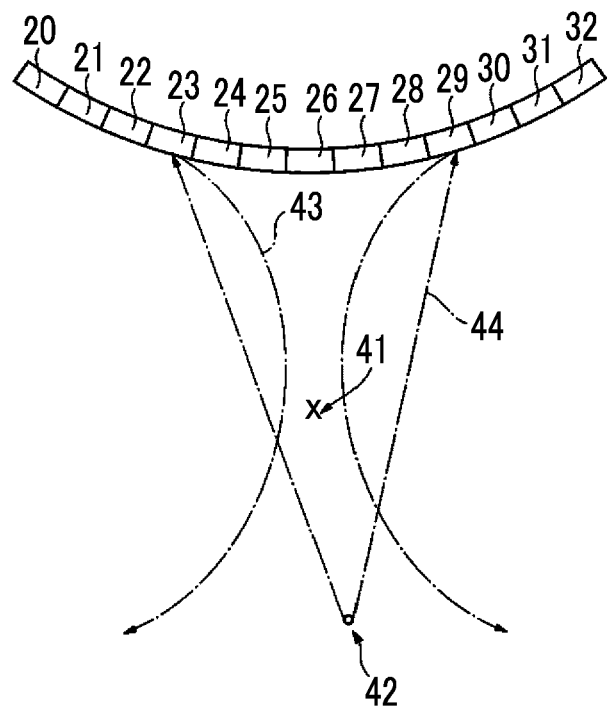
FIG. 14A shows transmission and reception of ultrasound waves.
Figure 15A:
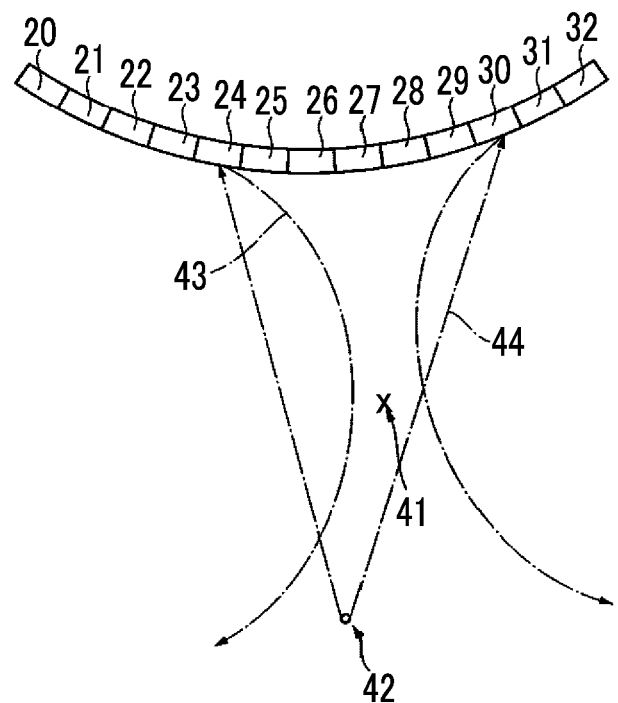
FIG. 15A shows transmission and reception of ultrasound waves.
Figure 16A:
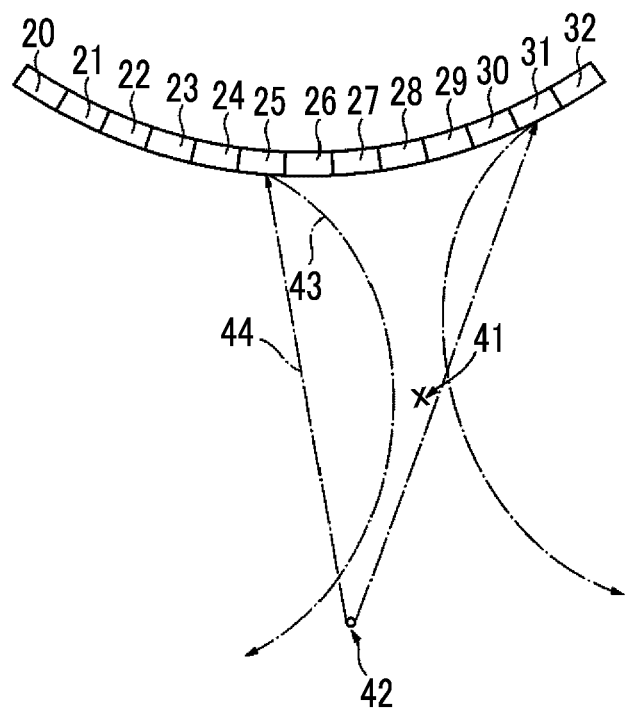
FIG. 16A shows transmission and reception of ultrasound waves.

FIGS. 12A, 13A, 14A, 15A, and 16A correspond to FIGS. 3A, 4A, 5A, 6A, and FIG. 7A described above. FIG. 12A shows a state in which the ultrasound pulse 43 is output from ultrasound transducers 21 to 27 among the ultrasound transducers 20 to 32 included in the ultrasound probe 6. FIG. 13A shows a state in which the ultrasound pulse 43 is output from ultrasound transducers 22 to 28 among the ultrasound transducers 20 to 32 included in the ultrasound probe 6. FIG. 14A shows a state in which the ultrasound pulse 43 is output from ultrasound transducers 23 to 29 among the ultrasound transducers 20 to 32 included in the ultrasound probe 6. FIG. 15A shows a state in which the ultrasound pulse 43 is output from ultrasound transducers 24 to 30 among the ultrasound transducers 20 to 32 included in the ultrasound probe 6. FIG. 16A shows a state in which the ultrasound pulse 43 is output from ultrasound transducers 25 to 31 among ultrasound transducers 20 to 32 included in the ultrasound probe 6.

Referring to FIG. 14A, it is assumed that the ultrasound pulse 43 is transmitted from the ultrasound transducers 23 to 29 as in FIG. 5A. The ultrasound pulse 43 is transmitted from the ultrasound transducers 23 to 29 so as to converge on the focusing position 41 at a predetermined distance in the transmission direction of the ultrasound transducer 26 (in FIG. 14A, directly below the ultrasound transducer 26) located at the center of the ultrasound transducers 23 to 29. In the example shown in FIG. 14A, the observation target position 42 is present in an arc direction by 0.5 ultrasound transducer from the extension direction of the central ultrasound transducer 26 and the focusing position 41. In a case where the ultrasound pulse 43 is emitted to the observation target position 42, the ultrasound echo 44 is generated from the observation target position 42. The ultrasound echo 44 is received by the ultrasound transducers 23 to 29.

Figure 14B:
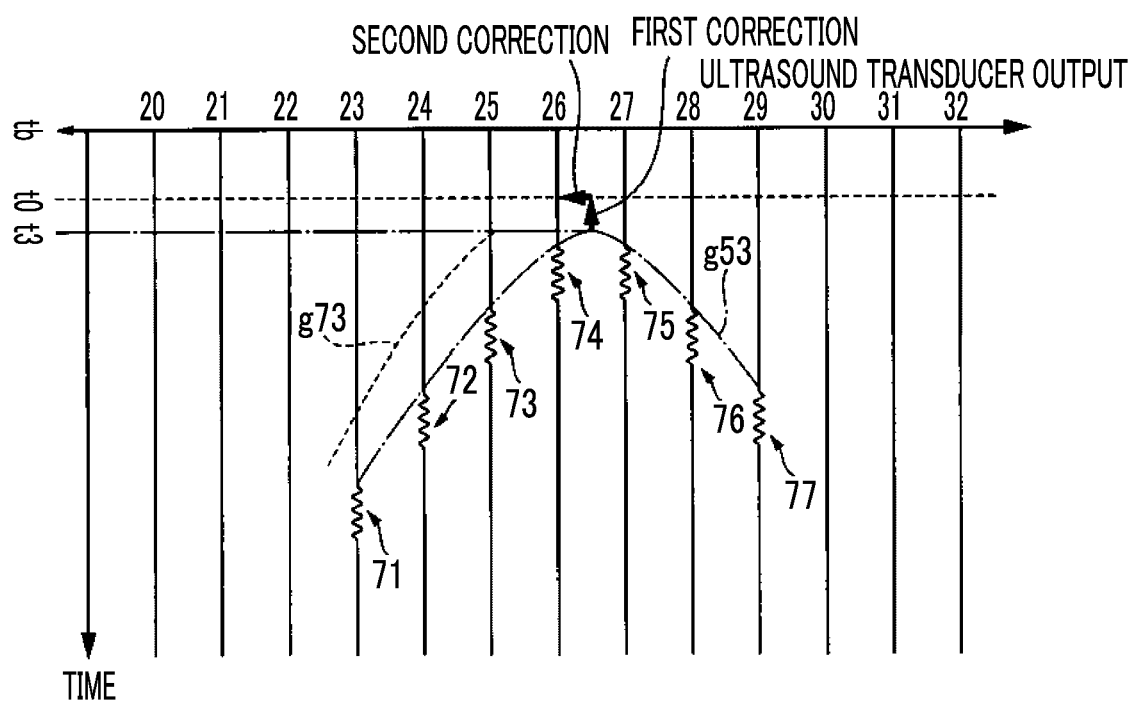
FIG. 14B shows an ultrasound echo signal.

FIG. 14B shows an ultrasound echo signal group g53 output from the ultrasound transducers 23 to 29 that receive the ultrasound echo 44. The ultrasound echo signal group g53 is also an envelope of ultrasound echo signals 71 to 77 output from the ultrasound transducers 23 to 29, respectively. Since the observation target position 42 is present in the output direction of the ultrasound pulse 43 between the ultrasound transducers 26 and 27 among the ultrasound transducers 23 to 29 that receive the ultrasound echo 44, the ultrasound echo signals 74 and 75 are first output from the ultrasound transducers 26 and 27 (time t3). Then, the ultrasound echo signals 73 and 76 are output from the ultrasound transducers 25 and 28, and then the ultrasound echo signals 72 and 77 are output from the ultrasound transducers 24 and 29. Finally, the ultrasound echo signal 71 is output from the ultrasound transducer 23.

Referring to FIG. 12A, it is assumed that the ultrasound pulse 43 is transmitted from the ultrasound transducers 21 to 27. The ultrasound echo 44 is received by the ultrasound transducers 21 to 27.

Figure 12B:
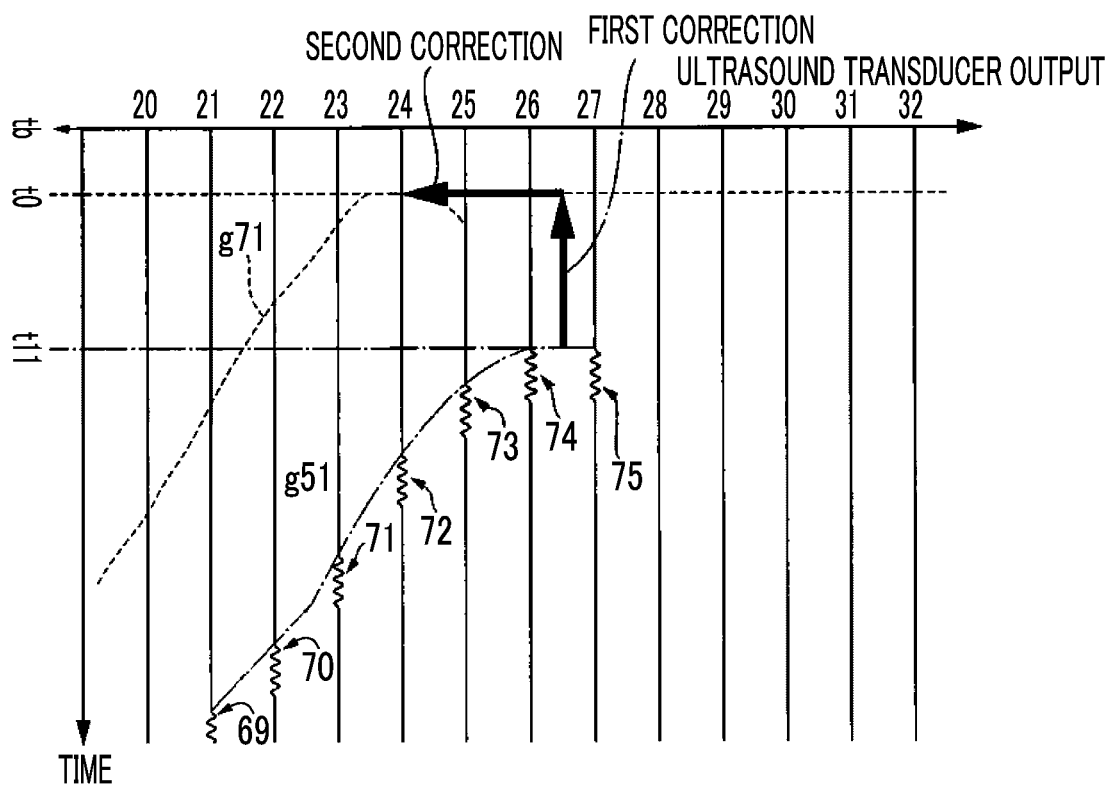
FIG. 12B shows an ultrasound echo signal.

Referring to FIG. 12B, the ultrasound echo signal group g51 is obtained from the ultrasound transducers 21 to 27. The ultrasound echo signal group g51 is also an envelope of ultrasound echo signals 69 to 75 output from the ultrasound transducers 21 to 27. In the same manner as described above, the ultrasound echo signals 74 and 75 are first output from the ultrasound transducers 26 and 27 (time t11).

Referring to FIG. 13A, it is assumed that ultrasound transducers to be driven are updated and the ultrasound pulse 43 is transmitted from the ultrasound transducers 22 to 28. The ultrasound echo 44 from the observation target position 42 is received by the ultrasound transducers 22 to 28.

Figure 13B:
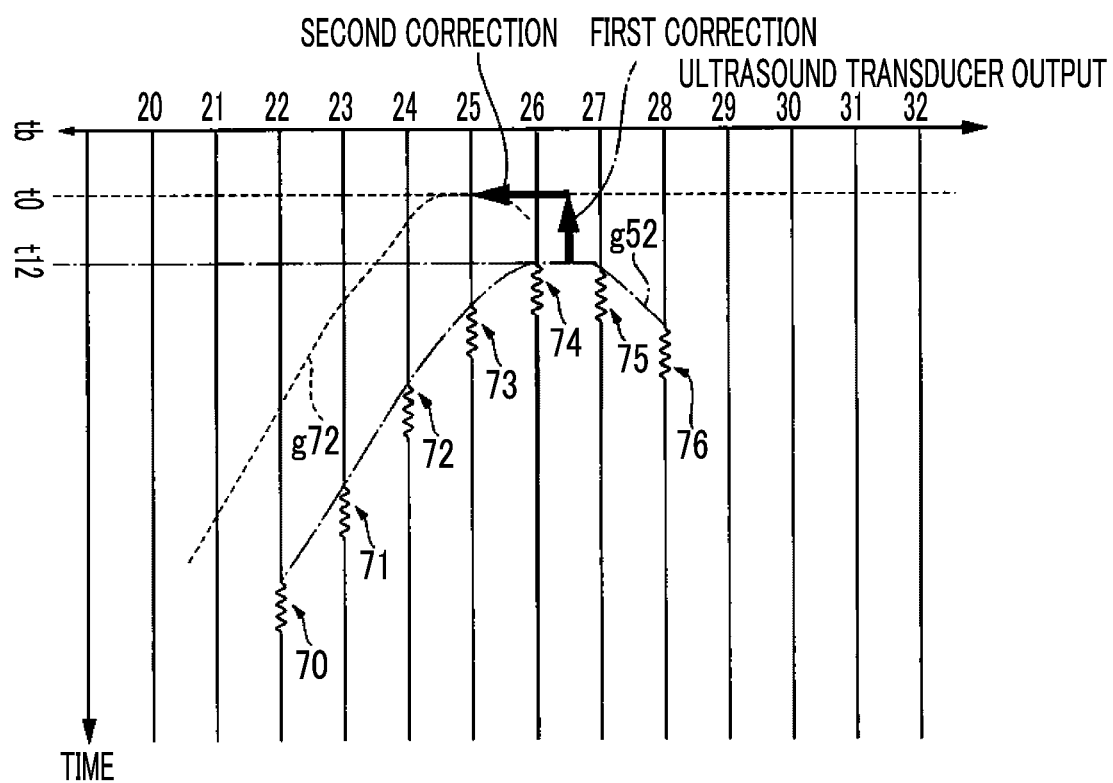
FIG. 13B shows an ultrasound echo signal.

Referring to FIG. 13B, the ultrasound echo signal group g52 is obtained from the ultrasound transducers 22 to 28. The ultrasound echo signal group g52 is also an envelope of ultrasound echo signals 70 to 76 output from the ultrasound transducers 22 to 28. In the same manner as described above, the ultrasound echo signals 74 and 75 are first output from the ultrasound transducers 26 and 27 (time t12).

In a case where ultrasound transducers to be driven are updated and the ultrasound pulse 43 is transmitted from the ultrasound transducers 23 to 29 as shown in FIG. 14A, the operation is the same as that already described with reference to FIGS. 14A and 14B.

Referring to FIG. 15A, it is assumed that ultrasound transducers to be driven are updated and the ultrasound pulse 43 is transmitted from the ultrasound transducers 24 to 30. In the same manner as described above, the ultrasound echo 44 is received by the ultrasound transducers 24 to 30.

Figure 15B:
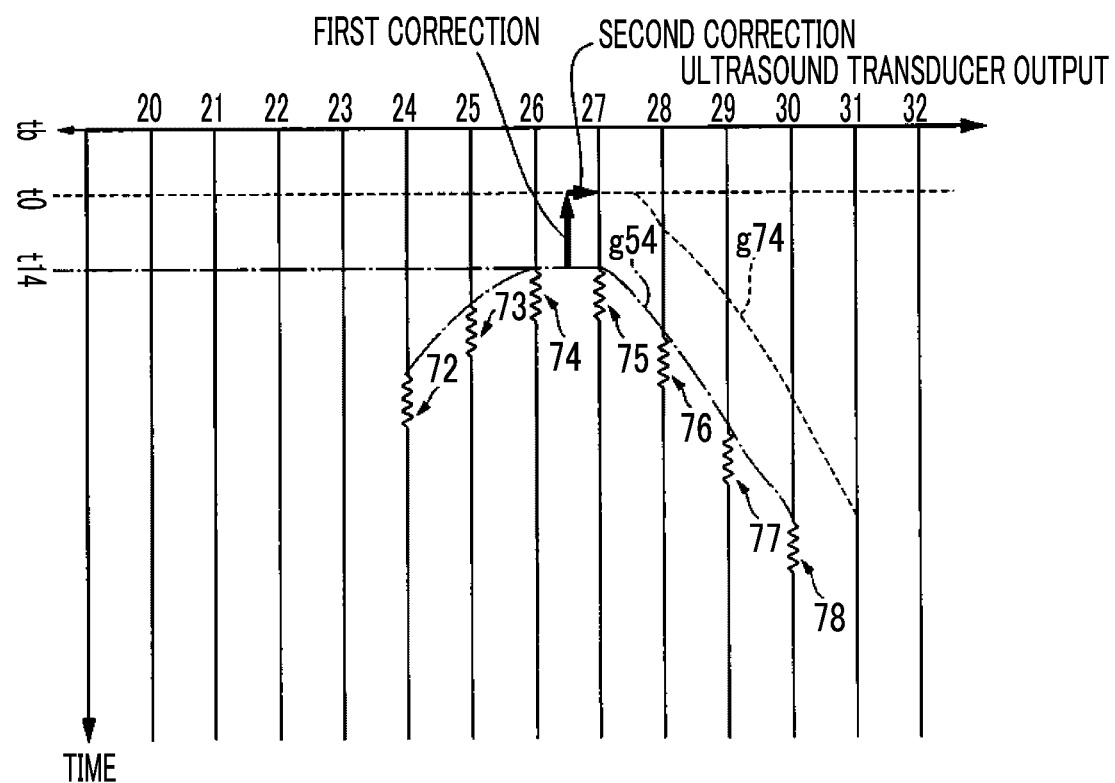
FIG. 15B shows an ultrasound echo signal.

Referring to FIG. 15B, the ultrasound echo signal group g54 is obtained from the ultrasound transducers 24 to 30. The ultrasound echo signal group g54 is also an envelope of ultrasound echo signals 72 to 78 output from the ultrasound transducers 24 to 30. In the same manner as described above, the ultrasound echo signals 74 and 75 are first output from the ultrasound transducers 26 and 27 (time t14).

Referring to FIG. 16A, it is assumed that ultrasound transducers to be driven are updated and the ultrasound pulse 43 is transmitted from the ultrasound transducers 25 to 31. The ultrasound echo 44 is received by the ultrasound transducers 25 to 31.

Figure 16B:
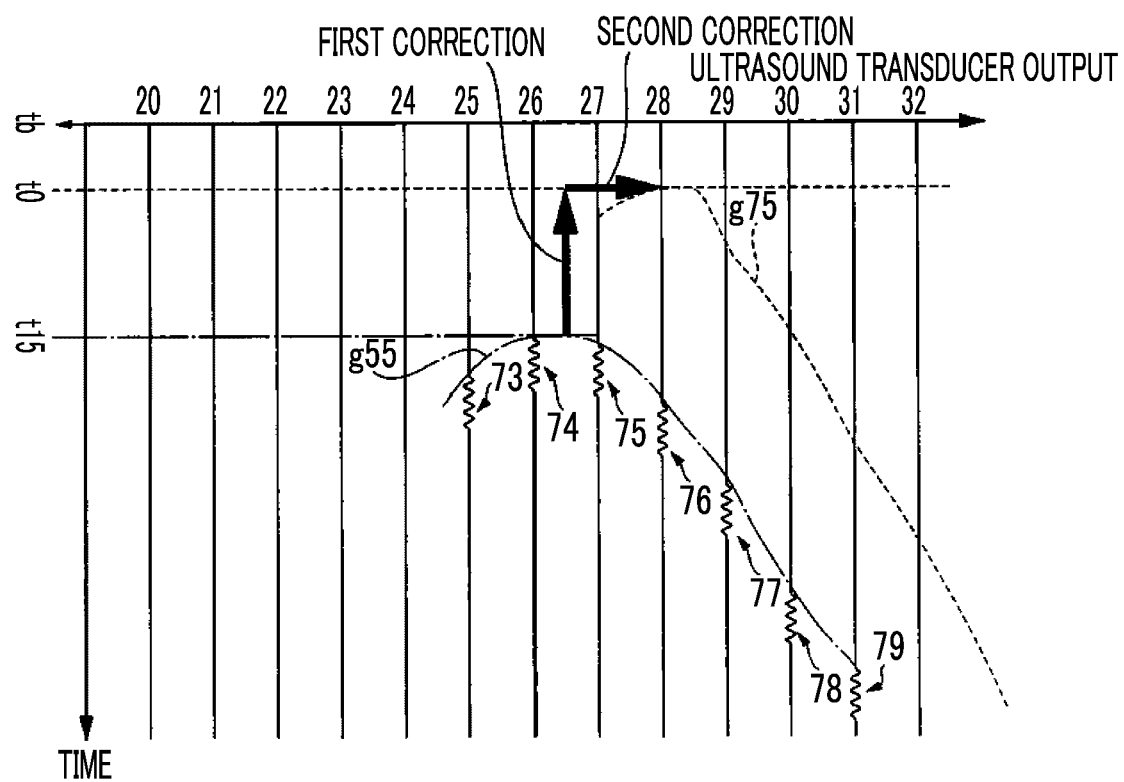
FIG. 16B shows an ultrasound echo signal.

Referring to FIG. 16B, the ultrasound echo signal group g55 is obtained from the ultrasound transducers 25 to 31. The ultrasound echo signal group g55 is also an envelope of ultrasound echo signals 73 to 79 output from the ultrasound transducers 25 to 31. In the same manner as described above, the ultrasound echo signal 74 is first output from the ultrasound transducer 26 (time t15).

Referring back to FIG. 2, the ultrasound echo signals obtained as described above are supplied to the reception device 7. The ultrasound echo signal is amplified by the reception device 7, and is converted into digital ultrasound echo data by the analog/digital (A/D) conversion circuit 8. The ultrasound echo data is supplied to the ultrasound echo data storage device 9 so as to be temporarily stored therein. The ultrasound echo data is read from the ultrasound echo data storage device 9, and is input to the ultrasound echo data processing device 10.

In the ultrasound echo data processing device 10, among ultrasound echo signals (acoustic wave echo signals) that are output from ultrasound transducers (acoustic wave transducers) due to the ultrasound transducers (acoustic wave transducers) receiving the ultrasound echo (acoustic wave echo) of the observation target position 42 of the subject obtained based on the driving of the ultrasound transducers (acoustic wave transducers) by the control device 2 (the driving device), as shown in FIGS. 12A, 13A, 14A, 15A, and 16A, for ultrasound echo data (acoustic wave signal) having a positional deviation in the arc direction between the focusing position 41 and the observation target position 42, the positional deviation is corrected according to the position of the ultrasound transducer to be driven.

In the same manner as described above, referring to FIG. 12B, in the ultrasound echo data processing device 102, first correction is performed in order to correct the delay time so that the ultrasound echo signal group g51 is output from the ultrasound transducer 24 at the time t0, and second correction is performed in order to shift the apex of the ultrasound echo signal group g51 so that the positional deviation in the arc direction between the focusing position 41 and the observation target position 42 is eliminated. The positional deviation in the arc direction is a deviation between the focusing position 41 and the observation target position 42 in the arc direction. The correction of the positional deviation in the arc direction is to generate an ultrasound echo signal, which can be obtained in a case where there is no positional deviation in the arc direction, in a case where there is a positional deviation in the arc direction between the focusing position 41 and the observation target position 42 as shown in FIG. 12A. In the case shown in FIG. 12A, the focusing position 41 and the observation target position 42 are shifted from each other by a distance of 2.5 ultrasound transducers in the arc direction. Accordingly, the ultrasound echo signal group g51 is shifted by the distance of 2.5 ultrasound transducers in a direction opposite to the arc direction (a direction from the ultrasound transducer 20 to the ultrasound transducer 32 is defined as the arc direction) so that the deviation of the distance is eliminated. A combination of the first correction and the second correction is positional deviation correction. Therefore, as shown in FIG. 12B, the ultrasound echo signal group g51 is corrected to an ultrasound echo data group g71 as shown by the dotted line. Thus, in the ultrasound echo data processing device 102, among the pieces of ultrasound echo data that are output from the ultrasound transducers 21 to 27 due to the ultrasound transducers 21 to 27 receiving the ultrasound echo of the observation target position 42 of the subject obtained based on the driving of the ultrasound transducers by the control device (the driving device) 2, for ultrasound echo data having a positional deviation in the arc direction between the focusing position 41 and the observation target position 42, the positional deviation is corrected according to the position of the ultrasound transducer to be driven by the control device 2.

Similarly, for the ultrasound echo data groups g52, g53, g54, and g55 in which a positional deviation in the arc direction occurs between the focusing position 41 and the observation target position 42 as in FIGS. 13B, 14B, 15B, and 16B, positional deviation correction is performed by the ultrasound echo data processing device 10, and ultrasound echo data groups g72, g73, g74, and g75 for which the positional deviation has been corrected are obtained.

The ultrasound echo data groups g71, g72, g73, g74, and g75 for which the positional deviation has been corrected are superimposed by the ultrasound echo data processing device 10, and the superimposed pieces of ultrasound echo data 69 to 79 are obtained. In the superimposition, superimposition is performed so that the position between the ultrasound transducers 26 and 27 on the extension line of the observation target position 42 overlaps the position between the pieces of ultrasound echo data 74 and 75. The superimposed pieces of ultrasound echo data 69 to 79 are supplied to the phasing addition device 11.

Figure 17:
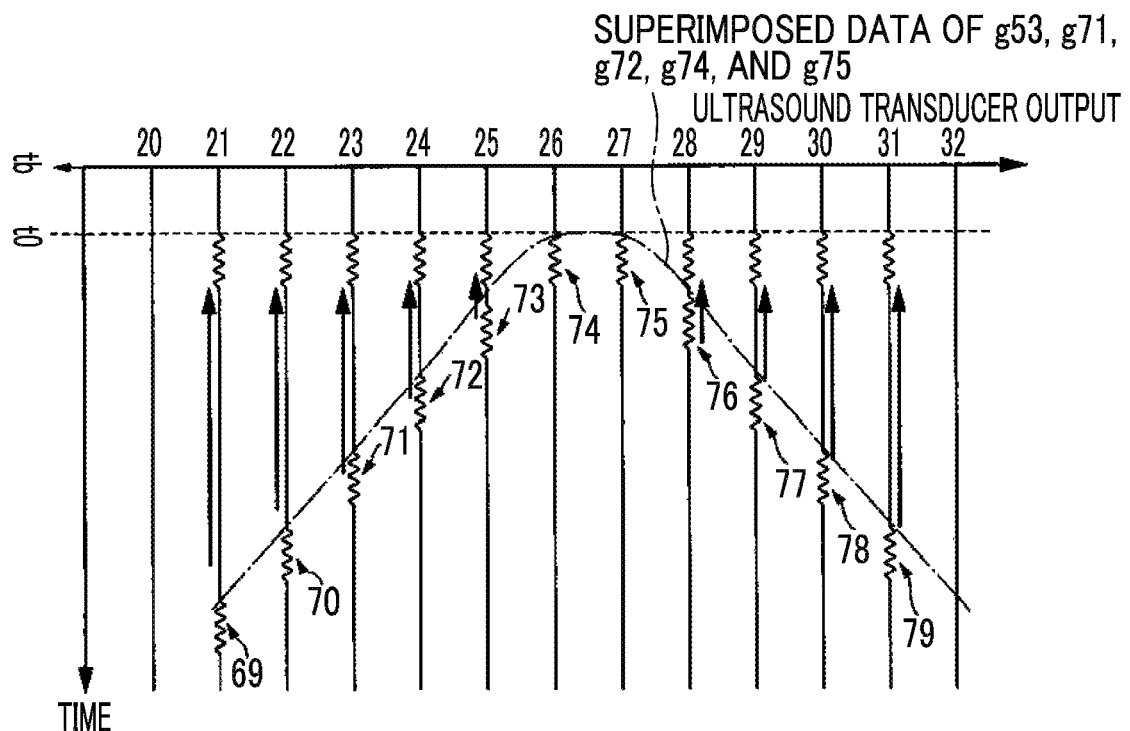
FIG. 17 shows a part of processing for phasing addition.
Figure 18:
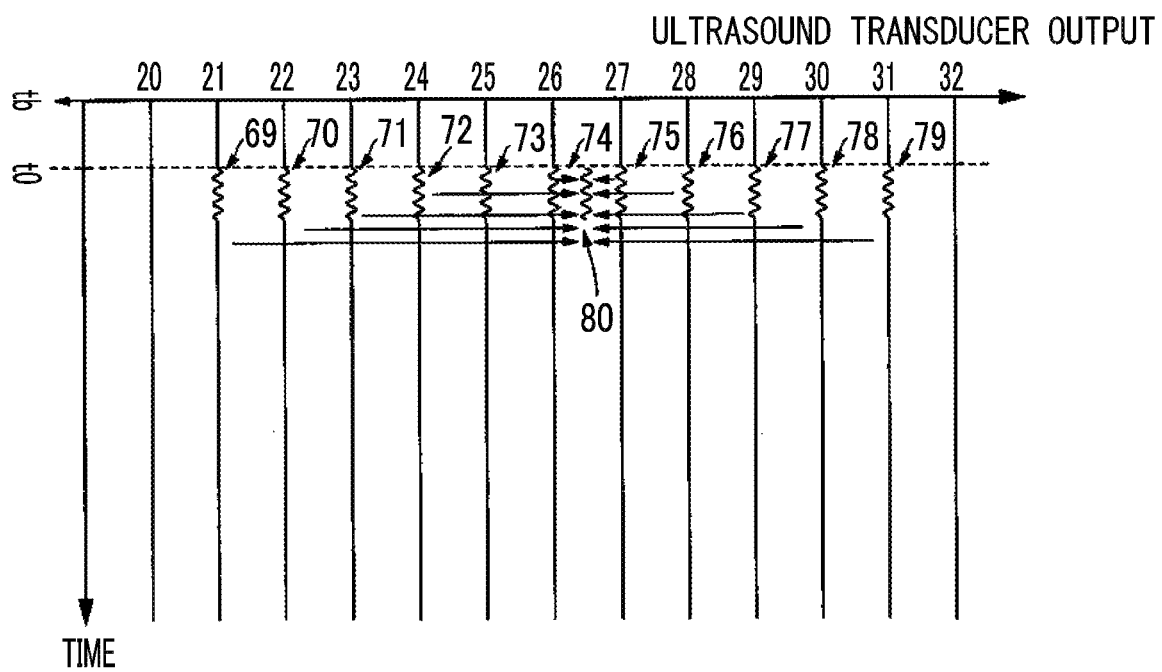
FIG. 18 shows a part of processing for phasing addition.

FIGS. 17 and 18 correspond to FIGS. 10 and 11, respectively, and show a state in which the superimposed pieces of ultrasound echo data 69 to 79 are subjected to phasing addition.

Referring to FIG. 17, output time correction is performed by the phasing addition device 11 so that the output time of the superimposed pieces of ultrasound echo data 69 to 79 becomes the same as the output timing of the virtual ultrasound echo signal that is first output from the virtual position between the ultrasound transducers 26 and 27 at time to.

Referring to FIG. 18, the pieces of ultrasound echo data 69 to 79 having been subjected to the output time correction are added up by the phasing addition device 11 so as to be superimposed at the position between the ultrasound transducers 26 and 27 on the extension line of the observation target position 42. By this addition, ultrasound echo data 80 indicating an interpolation scanning line (in this case, an interpolation scanning line corresponding to the position between the ultrasound transducers 26 and 27) is obtained.

The output time correction shown in FIG. 17 and the addition of the pieces of ultrasound echo data 69 to 79 shown in FIG. 18 are the phasing addition. By performing the phasing addition, the S/N ratio is improved.

Also in this case, the phasing addition shown in FIGS. 17 and 18 is performed after superimposition. However, the ultrasound echo data groups g71, g72, g73, g74, and g75 for which the positional deviation has been corrected may be subjected to phasing addition independently and then be superimposed to obtain a piece of superimposed data. In addition, at least some of the ultrasound echo data groups g71, g72, g73, g74, and g75 for which the positional deviation has been corrected may be superimposed after being weighted by the ultrasound echo data processing device 10 or the like.

Since the phasing addition is performed in this manner, the interpolation scanning line L2 indicating the ultrasound image Img is generated, as shown in FIG. 1, using the ultrasound echo data processing device 10 and the phasing addition device 11 (the interpolation scanning line generation device). In the example described above, the interpolation scanning line L2 corresponding to the position between the ultrasound transducers 26 and 27 is generated. The interpolation scanning lines L2 at other positions are similarly generated.

In the present embodiment, in the multi-line processing, the first interpolation scanning line L2 located between the real scanning lines L1 indicating the ultrasound image (acoustic wave image) Img of the subject generated using ultrasound echo data indicating the ultrasound echo 44 from the observation target position 42 of the subject obtained based on the driving of the ultrasound transducer is generated by the ultrasound echo data processing device 10 and the phasing addition device 11 (the interpolation scanning line generation device) for a portion deeper than the depth threshold value D1. As described above, the first interpolation scanning line L2 is generated from the ultrasound echo data groups g51, g52, g53, g54, and g55 having positional deviations in the are direction between the focusing position 41 and the observation target position. In order to generate the first interpolation scanning line L2 for a portion deeper than the depth threshold value D1, the multi-line processing described above may be performed using the ultrasound echo 44 obtained from the observation target position 42 deeper than the depth threshold value D1. Whether or not the ultrasound echo 44 is obtained from the observation target position 42 deeper than the depth threshold value D1 can be determined by using the time until the ultrasound wave output from the ultrasound transducer is transmitted to the observation target position 42 and the ultrasound echo 44 is received by the ultrasound transducer. By using the ultrasound echo data obtained as described above based on the ultrasound echo 44 obtained for a time longer than the time obtained in a case where the observation target position 42 is at the depth threshold value D1, it is possible to generate the first interpolation scanning line L2 at a position deeper than the depth threshold value D1. The time obtained in a case where the observation target position 42 is based on the depth threshold value D1 is obtained by time=(distance from the ultrasound transducer to the observation target position 42 through the focusing position 41+distance from the observation target position 42 to the ultrasound transducer that receives the ultrasound wave)/(speed of sound in the subject).

Referring to FIG. 2, the ultrasound echo data for generating the real scanning line L1 and the ultrasound echo data for generating the first interpolation scanning line L2 are input to a digital scan converter (DSC) 13.

The DSC 13 performs raster conversion into image data according to the scanning method of a normal television signal. For a portion shallower than the depth threshold value D1, the ultrasound image Img is generated from the real scanning line L1. For a portion deeper than the depth threshold value D1, image data indicating the ultrasound image Img as shown in FIG. 1 is obtained from the real scanning line L1 and the first interpolation scanning line L2 (DSC 13: the acoustic wave image generation device).

The image data output from the DSC 13 is subjected to image processing, such as gradation processing, by an image generating device 14. The image data output from the image generating device 14 is supplied to a display control device 16, and the ultrasound image Img is displayed on the display screen of a display device 17. The image data output from the image generating device 14 is also supplied to an image memory 15, and the image data indicating the ultrasound image Imaging is stored in the image memory 15. By supplying the image data stored in the image memory 15 to the display control device 16, the ultrasound image Img is displayed on the display screen of the display device 17 (the acoustic wave image display control device).

In the embodiment described above, the so-called multi-line processing is used for the real scanning line L1. However, the so-called multi-line processing may not be used for the real scanning line L1. In a case where the multi-line processing is not used, the real scanning line L1 is generated using the ultrasound echo data group g53 having no positional deviation described above. In the embodiment described above, the real scanning line L1 is generated using the ultrasound echo data of both the ultrasound echo data groups g51, g52, g54, and g55 having positional deviation and the ultrasound echo data group g53 having no positional deviation. However, the real scanning line L1 may be generated using only the ultrasound echo data groups g51, g52, g54, and g55 having positional deviation.

Figure 19:
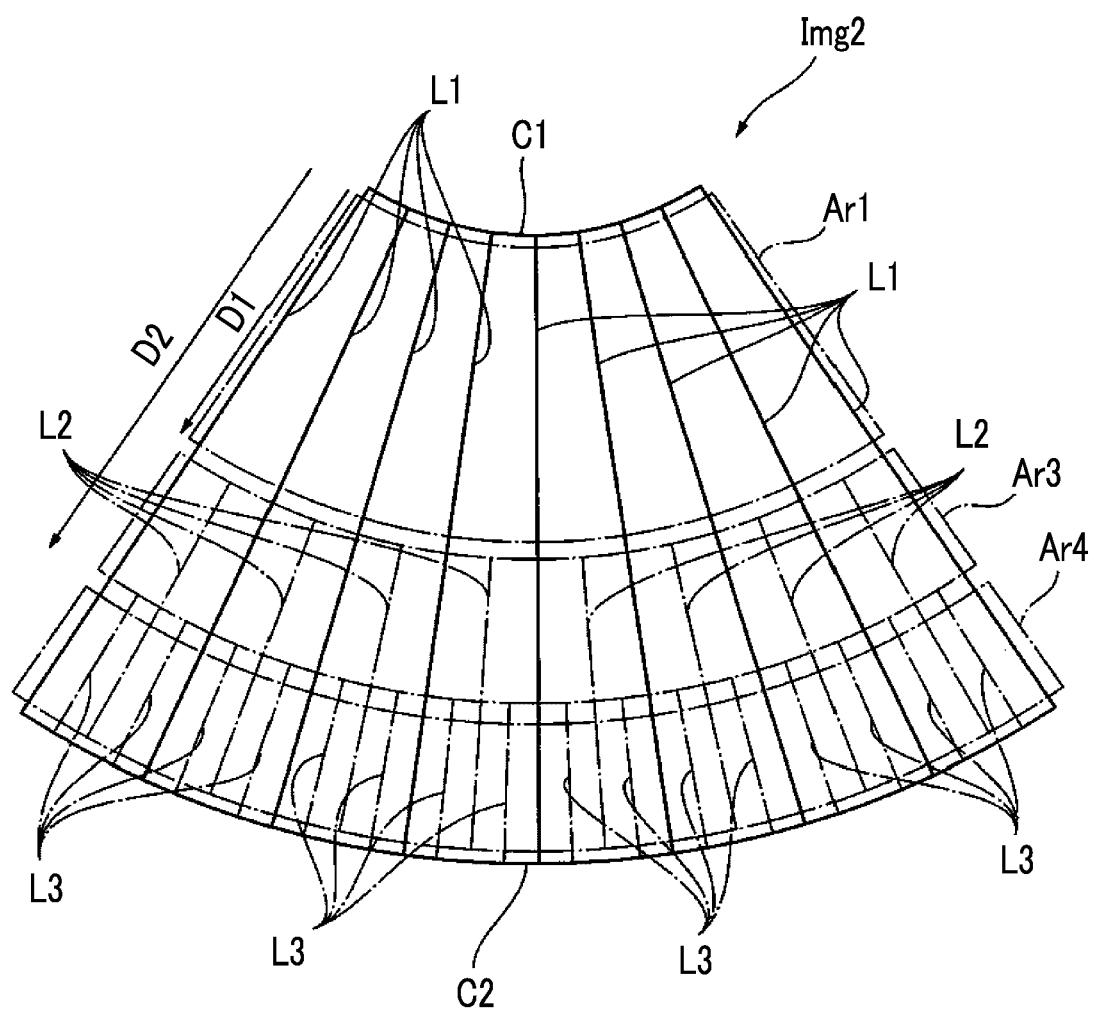
FIG. 19 is an example of an ultrasound image.

FIG. 19 shows another example of an ultrasound image Img2.

In the ultrasound image Img2 shown in FIG. 19, two depth threshold values D1 and D2 are defined. The second depth threshold value D2 is defined at a position deeper than the depth threshold value (first depth threshold value) D1.

A portion Ar1 of the ultrasound image Img2 at a depth equal to or less than (shallower than) the first depth threshold value D1 is formed by the real scanning line L1. Similarly to the ultrasound image Img shown in FIG. 1, a portion Ar3 of the ultrasound image Img2 that is deeper than the first depth threshold value D1 and less than (shallower than) the second depth threshold value D2 is formed by the real scanning line L1 and the first interpolation scanning line L2 located between the real scanning lines L1. A portion Ar4 of an ultrasound image Img3 at a depth equal to or less than (shallower than) the second depth threshold value D2 is formed by the real scanning line L1, the first interpolation scanning line L2, and a second interpolation scanning line L3.

For the sake of clarity, the first interpolation scanning line L2 and the second interpolation scanning line L3 are distinguished. However, since both the first interpolation scanning line L2 and the second interpolation scanning line L3 are located between the real scanning lines L1, the second interpolation scanning line L3 can also be referred to as the first interpolation scanning line L2. Therefore, it is possible to generate the first interpolation scanning line L2 (L3) having a different density for each depth so that the scanning line density is determined for each depth, and it is possible to generate the first interpolation scanning line L2 (L3) so that the scanning line density is fixed regardless of the depth of the subject.

Figure 20:
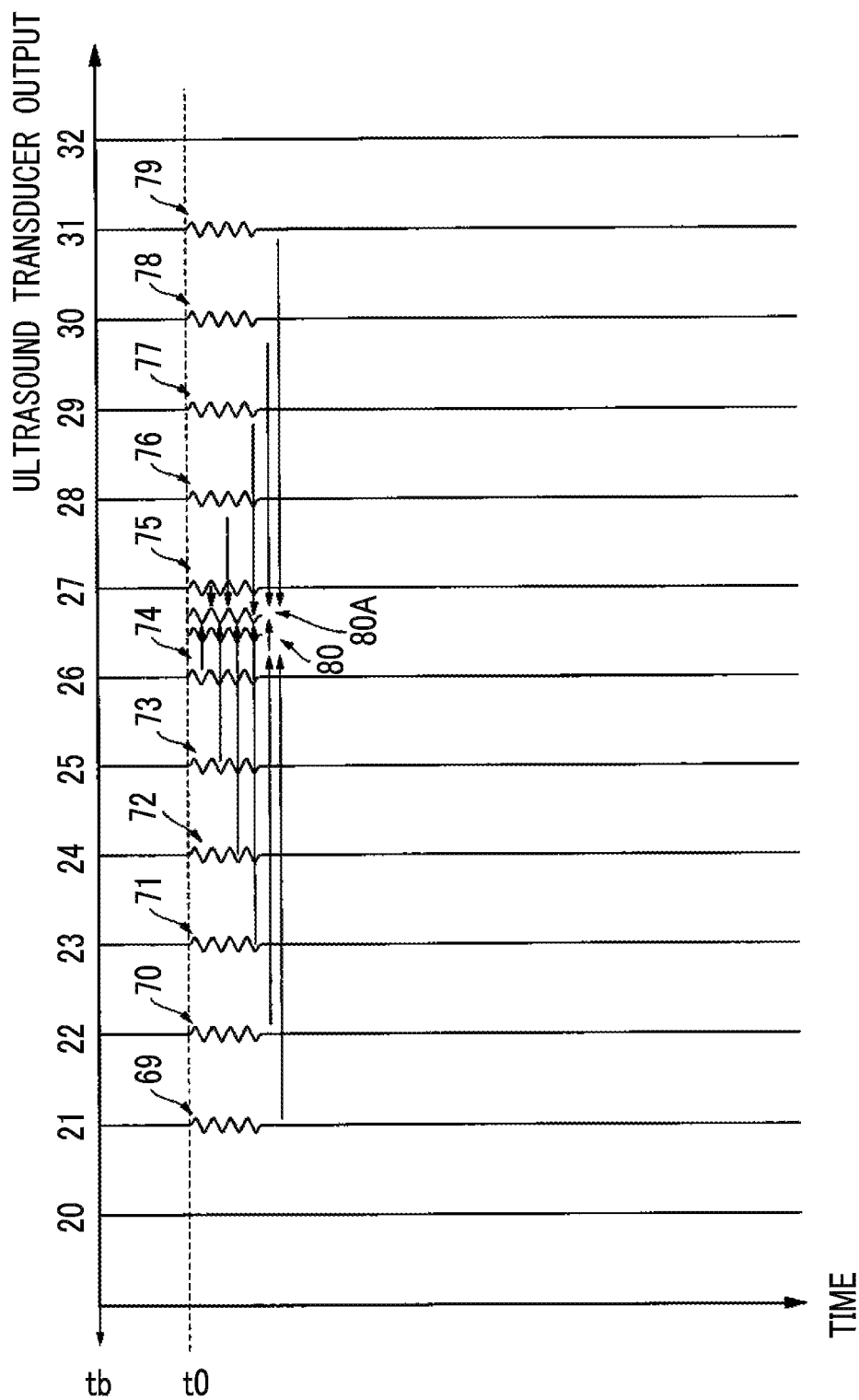
FIG. 20 shows how to generate a second interpolation scanning line.

FIG. 20 shows a method of generating the second interpolation scanning line L3, and corresponds to FIG. 18.

By using the ultrasound echo data 80 for generating the first interpolation scanning line L2 in addition to the ultrasound echo data 71 to 77 obtained as described above, ultrasound echo data 80A for generating the second interpolation scanning line L3 is generated. In the same manner as described above, the second interpolation scanning line L3 is digitally generated by the phasing addition device 11.

Figure 21:
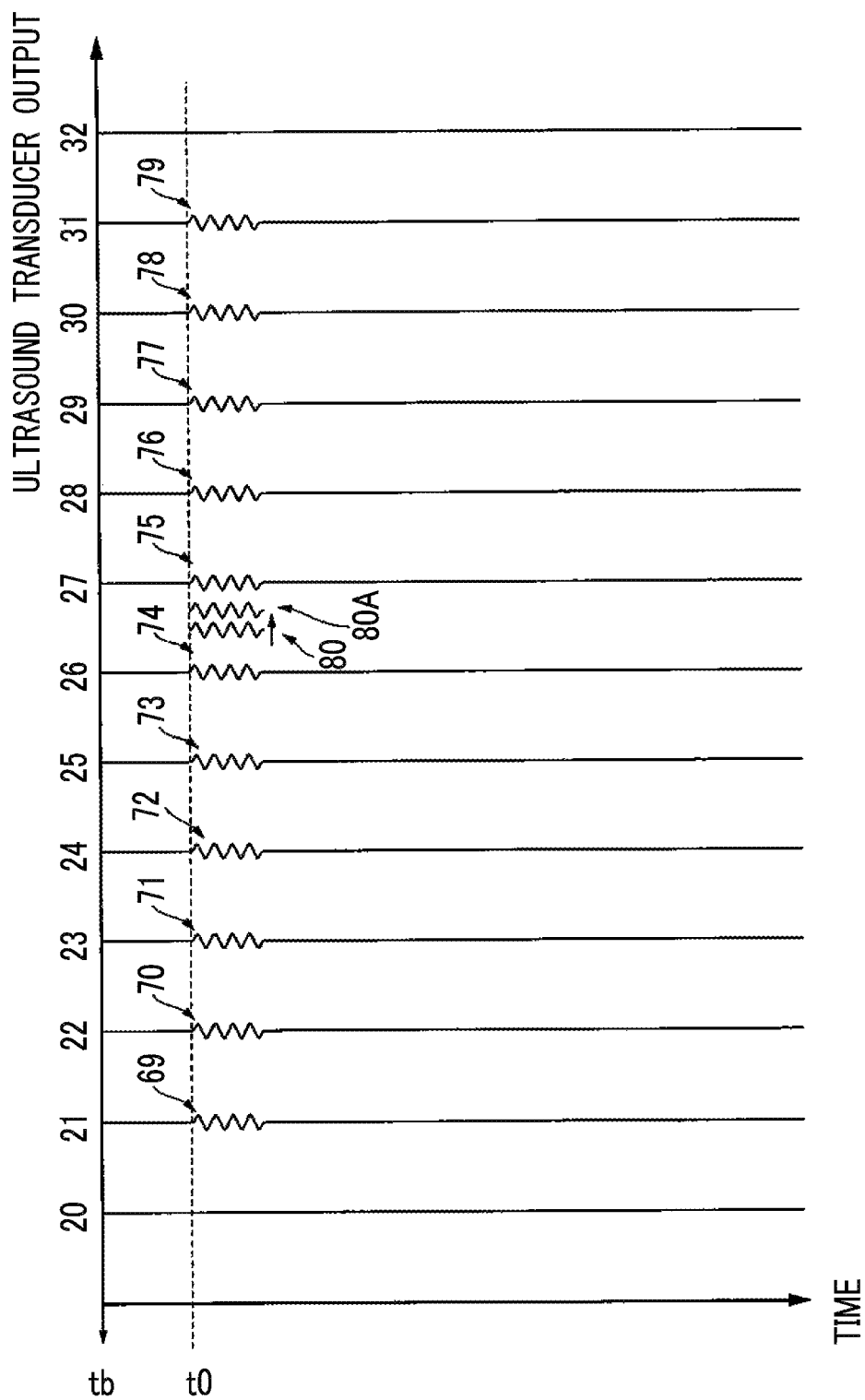
FIG. 21 shows how to generate a second interpolation scanning line.

FIG. 21 shows another method of generating the second interpolation scanning line L3.

By shifting the ultrasound echo data 80 for the first interpolation scanning line L2 generated as described above, the ultrasound echo data 80A for the second interpolation scanning line L3 described above is generated. In this manner, it is also possible to generate the second interpolation scanning line L3 using the already generated first interpolation scanning line L2. Such shift of the ultrasound echo data 80 can also be performed in the phasing addition device 11.

Figure 22:
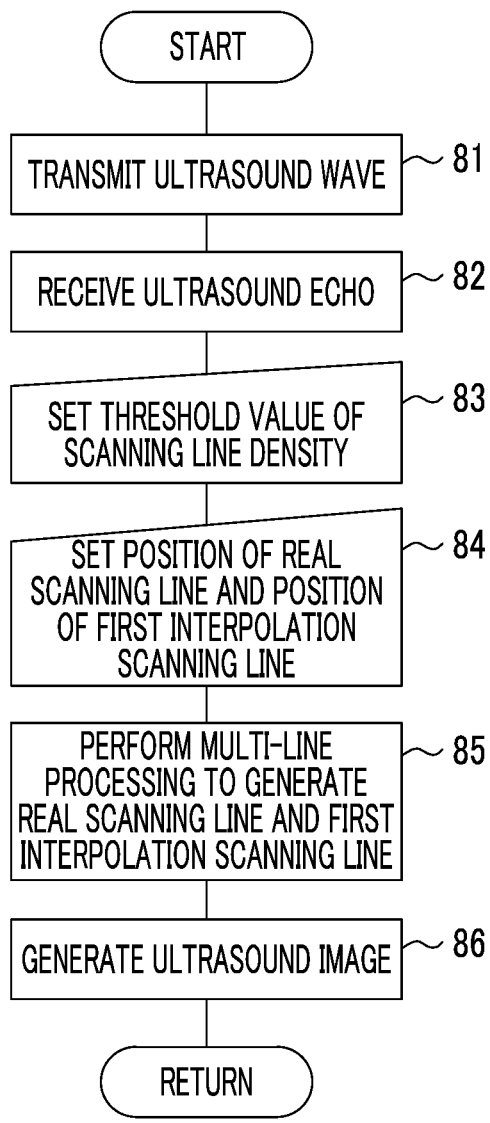
FIG. 22 is a flowchart showing the processing procedure of the ultrasound image generating apparatus.

FIG. 22 is a flowchart showing a processing procedure for generating an ultrasound image.

First, ultrasound waves are transmitted to the subject from the ultrasound transducer of the ultrasound probe 6 (step 81). The ultrasound echo 44 from the observation target position 42 of the subject is received by the ultrasound transducer of the ultrasound probe 6 (step 82). Then, the threshold value of the scanning line density is set using the operation device 3 (step 83), and the position of the real scanning line L1 and the position of the first interpolation scanning line L2 (and the second interpolation scanning line L3 if necessary) are set using the operation device 3 (step 84). The setting of the threshold value of the scanning line density and the setting of the position of the real scanning line L1 and the position of the first interpolation scanning line L2 (and the second interpolation scanning line L3 if necessary) may be performed before transmitting the ultrasound wave.

As described above, in the phasing addition device 11 (the interpolation scanning line generation device), the real scanning line L1 and the first interpolation scanning line L2 are generated so that the scanning line density becomes equal to or greater than the predetermined threshold value regardless of the depth of the subject (step 85). For example, as shown in FIG. 1, for the depth up to the first depth threshold value D1, the real scanning line L1 is generated for the first ultrasound image portion Ar1. For the second ultrasound image portion Ar2, the real scanning line L1 and one first interpolation scanning line L2 between the real scanning lines L1 are positioned and generated. The ultrasound image Img is generated using the real scanning line L1 and the first interpolation scanning line L2 generated as described above (step 86).

In steps 85 and 86, the case has been described in which the first interpolation scanning line L2 is set in two stages (one depth threshold value is set) in FIG. 1. However, the same can be done in a case where the depth direction is divided into three or more stages (two or more depth threshold values are set). For example, as shown in FIG. 19, similarly for the first ultrasound image portion Ar1 up to the first depth threshold value D1, the second ultrasound image portion Ar2 that is deeper than the first depth threshold value D1 and is up to the second depth threshold value D2, and the third ultrasound image portion Ar3 deeper than the second depth threshold value D2, the first interpolation scanning line L2 and the second interpolation scanning line L3 (and other interpolation scanning lines if necessary) are generated so that the density set for each portion is obtained (applied in step 85), and an ultrasound image is obtained (applied in step 86).

Figure 23:
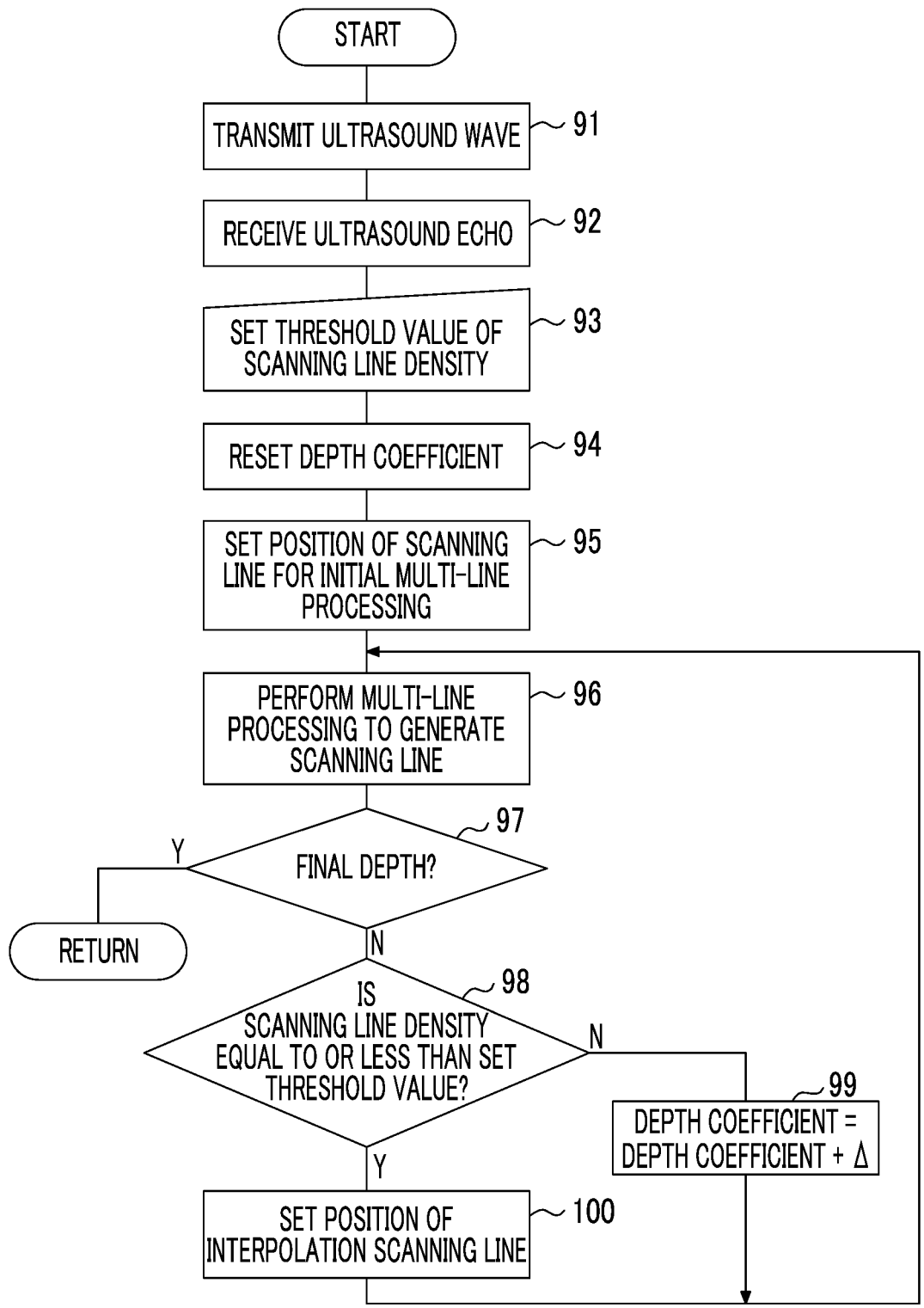
FIG. 23 is a flowchart showing the processing procedure of the ultrasound image generating apparatus.

FIG. 23 is a flowchart showing another processing procedure for generating an ultrasound image. In the processing procedure, the density of scanning lines (including the real scanning line L1, the first interpolation scanning line L2, and the second interpolation scanning line L3) is sequentially calculated for each depth. In a case where the calculated density is equal to or less than a predetermined threshold value, an interpolation scanning line is generated so that the calculated density becomes equal to or greater than the predetermined threshold value.

Ultrasound waves are transmitted from the ultrasound transducers of the ultrasound probe 6 (step 91), and the ultrasound echo 44 is received by the ultrasound transducers (step 92). A desired scanning line density is set using the operation device 3 (step 93). Then, a depth coefficient indicating the depth of the subject is reset to 0 (step 94), and the position of the scanning line for initial multi-line processing is set (step 95). In the initial multi-line processing, the real scanning line L1 is generated. Multi-line processing is performed, and the real scanning line L1 is generated by the ultrasound echo data processing device 10 as described above (step 96). If the calculated depth coefficient is the final depth of the subject generated in the ultrasound diagnostic apparatus 1 (YES in step 97), the process is ended. If the calculated depth coefficient is not the final depth of the subject generated in the ultrasound diagnostic apparatus 1 (NO in step 97), the scanning line density at the depth at which the real scanning line L1 is generated is calculated by the control device 2 (the scanning line density calculation device), and it is determined whether or not the calculated scanning line density is equal to or less than the set scanning line threshold value (step 98). If the calculated scanning line density is equal to or less than the set threshold value (YES in step 98), the positions of the interpolation scanning lines (the first interpolation scanning line L2 and the second interpolation scanning line L3) is set so that the density of the scanning lines is doubled (step 100). The interpolation scanning lines (the first interpolation scanning line L2 and the second interpolation scanning line L3) are generated by the multi-line processing (step 96). The processing from step 96 is repeated until the scanning line density becomes equal to or greater than the density at the set depth. If the scanning line density is equal to or greater than the density of the set threshold value (NO in step 98), a predetermined depth 4 is added to the depth coefficient for the calculation of the scanning line density and the generation of the interpolation scanning line at the next depth (step 99).

In the above processing, the case has been described in which the scanning line density is equal to or greater than the threshold value regardless of the depth. However, a different threshold value may be set for each depth, and interpolation scanning lines of different densities may be set and generated for different depths so that the scanning line density equal to or greater than the threshold value corresponding to the depth is obtained.

Figure 24:
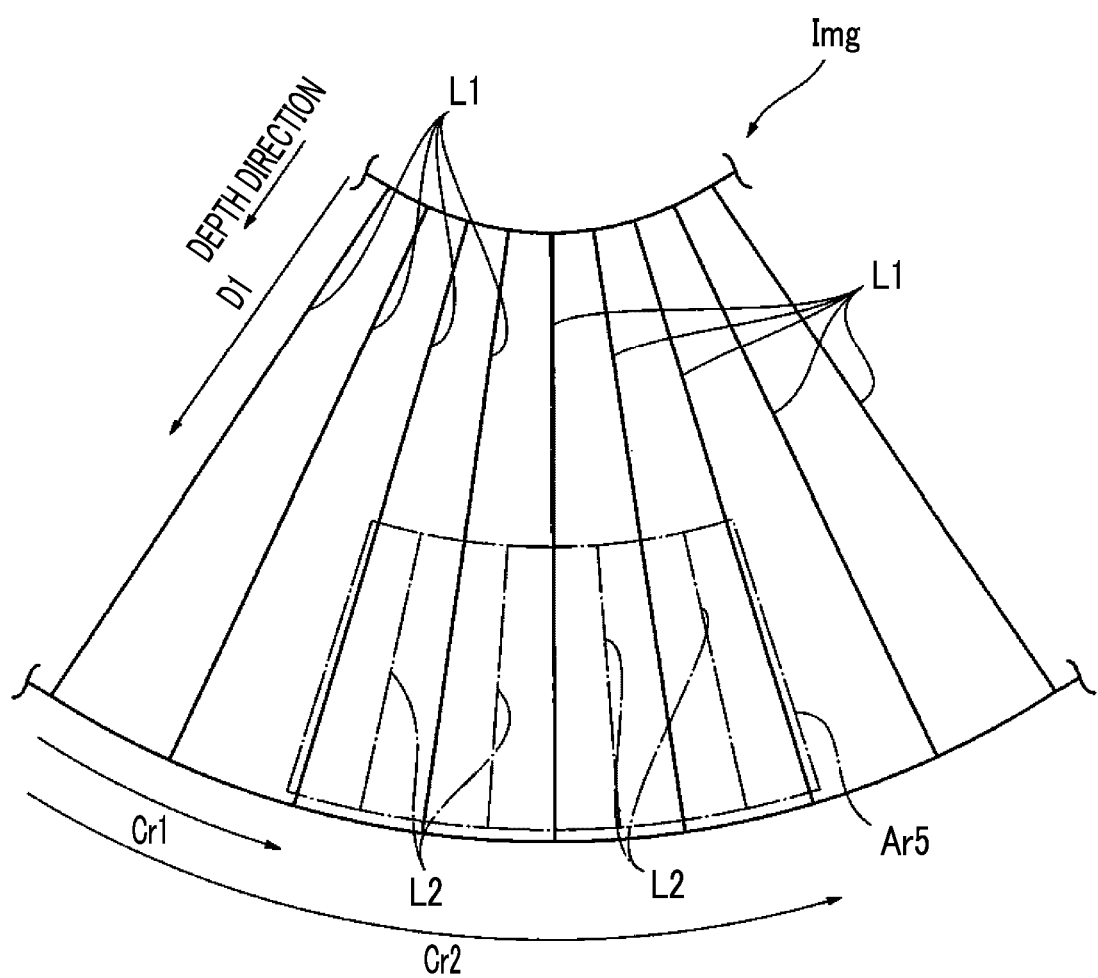
FIG. 24 is an example of an ultrasound image.
Figure 25:
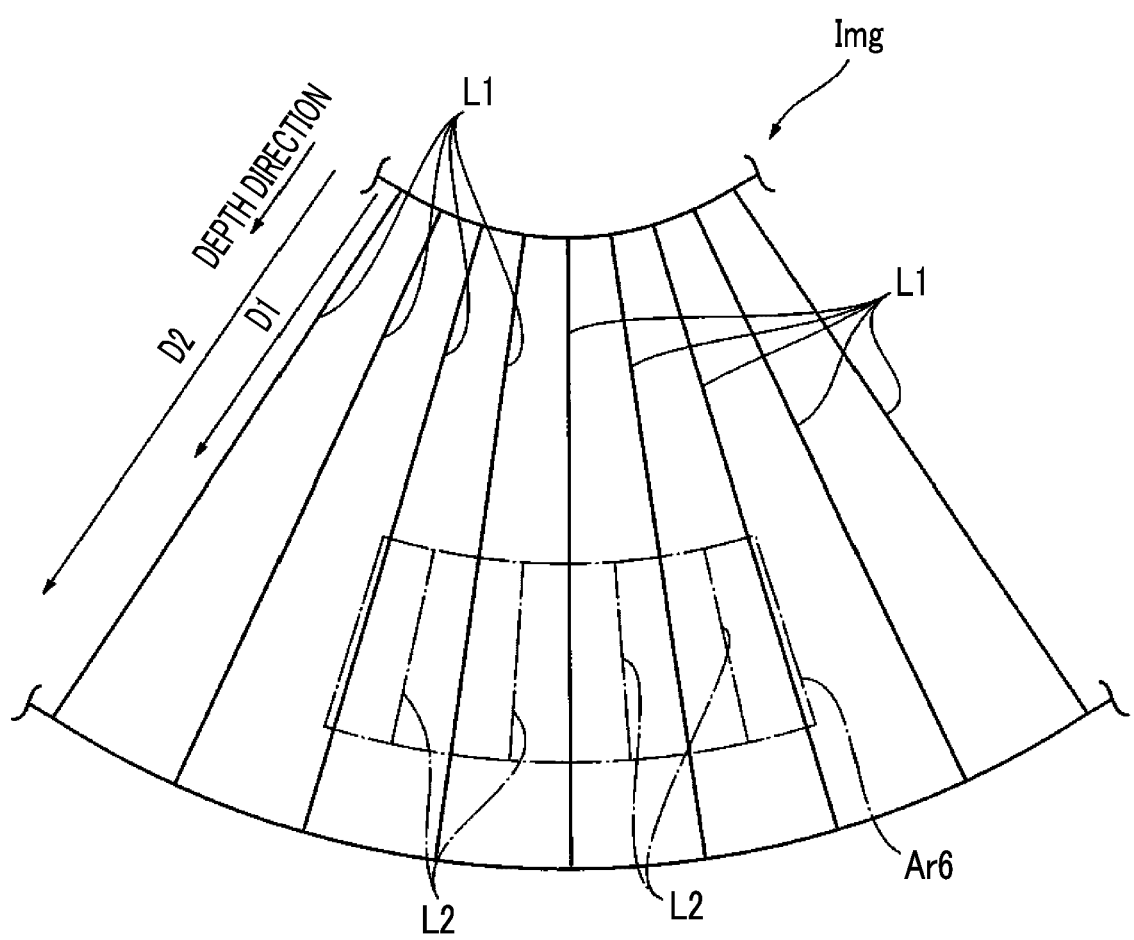
FIG. 25 is an example of an ultrasound image.

FIGS. 24 and 25 show a further modification example, and are an example of the ultrasound image Img.

In the ultrasound image Img2 shown in FIG. 24, instead of generating interpolation scanning lines for all portions of the ultrasound image at a position deeper than the depth threshold value D1, the interpolation scanning line L2 is generated in a portion Ar5 between a first threshold value Cr1 and a second threshold value Cr2 in the arc direction. Thus, the first interpolation scanning line L2 (and the second interpolation scanning line L3 if necessary) may be generated not only for the image portion determined in the depth direction but also for the image portion determined in the depth direction and the arc direction. Since the number of interpolation scanning lines to be generated is small, it is possible to shorten the time taken to generate the interpolation scanning lines. Accordingly, it is possible to shorten the time until the ultrasound image Img2 is displayed.

In the ultrasound image Img3 shown in FIG. 25, the interpolation scanning line L2 is generated in a portion Ar6 that is at a position deeper than the depth threshold value D1, is at a position shallower than the depth threshold value D2, and is between the first threshold value Cr1 and the second threshold value Cr2 in the arc direction. Thus, the interpolation scanning line L2 may be generated for a partial image portion of the ultrasound image Img3. Only a region in which the user is interested can be displayed as a more detailed ultrasound image.

What is claimed is:

1. An acoustic wave image generating apparatus, comprising:
an acoustic wave probe in which a plurality of acoustic wave transducers are arranged in an arc shape in an arc direction; and
a processor circuitry
for making the acoustic wave transducers transmit acoustic waves converging on a focusing position to a subject while updating the acoustic wave transducers for transmitting acoustic waves in a sequential manner;
for generating real scanning lines indicating an acoustic wave image of the subject using an acoustic wave echo signal indicating an acoustic wave echo from an observation target position of the subject that is obtained based on driving of the acoustic wave transducers by the processor circuitry;
for generating a first interpolation scanning line located between the first real scanning lines using the acoustic wave echo signal indicating the acoustic wave echo, which is obtained when there is a positional deviation in the arc direction between the focusing position and the observation target position, from the observation target position, for a portion deeper than a depth threshold value in the subject; and
for generating an acoustic wave image of the subject from the real scanning line and the first interpolation scanning line,
wherein the acoustic wave echo signal is shifted by a corresponding distance to correct for the positional deviation.

2. The acoustic wave image generating apparatus according to claim 1,
wherein the processor circuitry generates the second interpolation scanning line for a portion deeper than the depth threshold value in the subject using the acoustic wave echo signal, which is obtained from the portion deeper than the depth threshold value in the subject and which has a positional deviation in the arc direction between the focusing position and the observation target position.

3. The acoustic wave image generating apparatus according to claim 1, further comprising:
a processor circuitry for generating a second interpolation line, which is located between the first interpolation scanning line generated by the processor circuitry and the real scanning line, using the acoustic wave echo signal indicating the acoustic wave echo, which is obtained when there is a positional deviation in the arc direction between the focusing position and the observation target position, from the observation target position.

4. The acoustic wave image generating apparatus according to claim 1,
wherein the processor circuitry is further for generating a second interpolation line, which is located between the first interpolation scanning line generated by the processor circuitry and the real scanning line, from the real scanning line and the first interpolation scanning line generated by the processor circuitry.

5. The acoustic wave image generating apparatus according to claim 1,
wherein the processor circuitry is further for generating a second interpolation line, which is located between the first interpolation scanning line generated by the processor circuitry and the real scanning line, from the first interpolation scanning line generated by the processor circuitry.

6. The acoustic wave image generating apparatus according to claim 1, further comprising:
a scanning line density calculation device for calculating a scanning line density of the real scanning lines for each depth of the subject,
wherein the second real line generation device generates the first interpolation scanning line in a case where the scanning line density calculated by the scanning line density calculation device is equal to or less than a threshold value.

7. The acoustic wave image generating apparatus according to claim 1,
wherein the processor circuitry generates the first interpolation scanning line of a different density for each depth until a scanning line density determined for each depth of the subject is obtained.

8. The acoustic wave image generating apparatus according to claim 1, further comprising:
a scanning line density calculation device for calculating a scanning line density of the real scanning lines for each depth of the subject,
wherein the processor circuitry generates the first interpolation line whose scanning line density is equal to or greater than a threshold value regardless of the depth of the subject.

9. The acoustic wave image generating apparatus according to claim 1, further comprising:
an acoustic wave image display control device for displaying the acoustic wave image generated by the processor circuitry on a display device.

10. The acoustic wave image generating apparatus according to claim 3,
wherein the processor circuitry generates the acoustic wave image from the real scanning line, the first interpolation scanning line, and the third scanning line.

11. The acoustic wave image generating apparatus according to claim 1,
wherein the acoustic wave probe is a convex type acoustic wave probe.

12. The acoustic wave image generating apparatus according to claim 1,
wherein the real scanning line is generated using the acoustic wave echo signal indicating the acoustic wave echo, which is obtained when there is a positional deviation in the arc direction between the focusing position and the observation target position, from the observation target position.

13. The acoustic wave image generating apparatus according to claim 1,
wherein the real scanning line is generated from the acoustic wave echo signal indicating the acoustic wave echo, which is obtained when there is a positional deviation in the arc direction between the focusing position and the observation target position, from the observation target position, and the acoustic wave echo signal having no positional deviation.

14. A control method of an acoustic wave image generating apparatus comprising an acoustic wave probe in which a plurality of acoustic wave transducers are arranged in an arc shape in an arc direction, the method comprising:
making via processing circuitry, the acoustic wave transducers transmit acoustic waves converging on a focusing position to a subject while updating the acoustic wave transducers for transmitting acoustic waves in a sequential manner;
generating via the processing circuitry, real scanning lines indicating an acoustic wave image of the subject using an acoustic wave echo signal indicating an acoustic wave echo from an observation target position of the subject that is obtained based on driving of the acoustic wave transducers;
generating, via the processing circuitry, a first interpolation scanning line located between the real scanning lines using the acoustic wave echo signal indicating the acoustic wave echo, which is obtained when there is a positional deviation in the arc direction between the focusing position and the observation target position, from the observation target position, for a portion deeper than a depth threshold value in the subject; and
generating, via the processing circuitry, an acoustic wave image of the subject from the real scanning line and the first interpolation scanning line,
wherein the acoustic wave echo signal is shifted by a corresponding distance to correct for the positional deviation.

* * * * *